United States Patent [19]
Shturman

[11] Patent Number: 6,027,460
[45] Date of Patent: Feb. 22, 2000

[54] ROTATABLE INTRAVASCULAR APPARATUS

[75] Inventor: Leonid Shturman, Minnetonka, Minn.

[73] Assignee: Shturman Cardiology Systems, Inc., Minneapolis, Minn.

[21] Appl. No.: 08/527,932

[22] Filed: Sep. 14, 1995

[51] Int. Cl.[7] ...................................................... A61B 5/00
[52] U.S. Cl. ......................... 600/585; 600/129; 600/437; 604/95; 604/528; 606/129; 606/180; 607/122
[58] Field of Search ............................ 604/282, 95, 528; 606/180, 129; 600/585, 437; 607/122

[56] References Cited

U.S. PATENT DOCUMENTS

| | | |
|---|---|---|
| 4,573,470 | 3/1986 | Samson et al. . |
| 4,641,654 | 2/1987 | Samson et al. . |
| 4,664,113 | 5/1987 | Frisbie et al. . |
| 4,946,440 | 8/1990 | Hall . |
| 4,976,689 | 12/1990 | Buchbinder et al. . |
| 5,090,957 | 2/1992 | Moutafis et al. . |
| 5,114,403 | 5/1992 | Clarke et al. . |
| 5,217,474 | 6/1993 | Zacca et al. . |
| 5,246,420 | 9/1993 | Kraus et al. . |
| 5,273,052 | 12/1993 | Kraus et al. ............................. 128/772 |
| 5,308,354 | 5/1994 | Zecca et al. ............................. 606/159 |
| 5,312,427 | 5/1994 | Shturman ................................ 606/159 |
| 5,314,438 | 5/1994 | Shturman ................................ 606/159 |
| 5,356,418 | 10/1994 | Shturman ................................ 606/159 |
| 5,360,432 | 11/1994 | Shturman ................................ 606/159 |
| 5,429,604 | 7/1995 | Hammersmark et al. . |
| 5,454,787 | 10/1995 | Lundquist . |
| 5,501,694 | 3/1996 | Ressemann et al. .................... 606/159 |
| 5,554,163 | 9/1996 | Shturman ................................ 606/159 |
| 5,681,336 | 10/1997 | Clement et al. ........................ 606/159 |

FOREIGN PATENT DOCUMENTS 375775  7/1990  European Pat. Off. .

Primary Examiner—Mark Bockelman
Attorney, Agent, or Firm—Fredrikson & Byron, P.A.

[57] ABSTRACT

A rotatable intravascular apparatus having a flexible, elongated medical device and a mechanism for controlling the rotational orientation of the distal end of the medical device. The apparatus includes a flexible torquing sheath extending along a substantial length of the elongated medical device. The distal end of the torquing sheath is secured to the distal portion of the medical device, but not to the intermediate or proximal portions of the medical device, so that rotation of the proximal end of the torquing sheath with respect to the proximal portion of the medical device conveys torque to the distal end of the torquing sheath and, therefore, to the distal portion of the medical device, thereby rotating the distal portion of the medical device. By holding the proximal portion of the medical device and preventing the proximal portion from rotating while the distal portion is rotated by the torquing sheath, a certain amount of torque is built up along the length of the medical device; this torque tends to resist rotation of the distal portion of the medical device, and therefore provides a force which resists or dampens the tendency of the distal portion of the elongated medical device to "whip" when the torquing sheath is rotated. In a preferred embodiment the medical device is a guide wire, the torquing sheath being removable after the guide wire has been advanced, with the aid of the torquing sheath, to a location of interest.

25 Claims, 31 Drawing Sheets

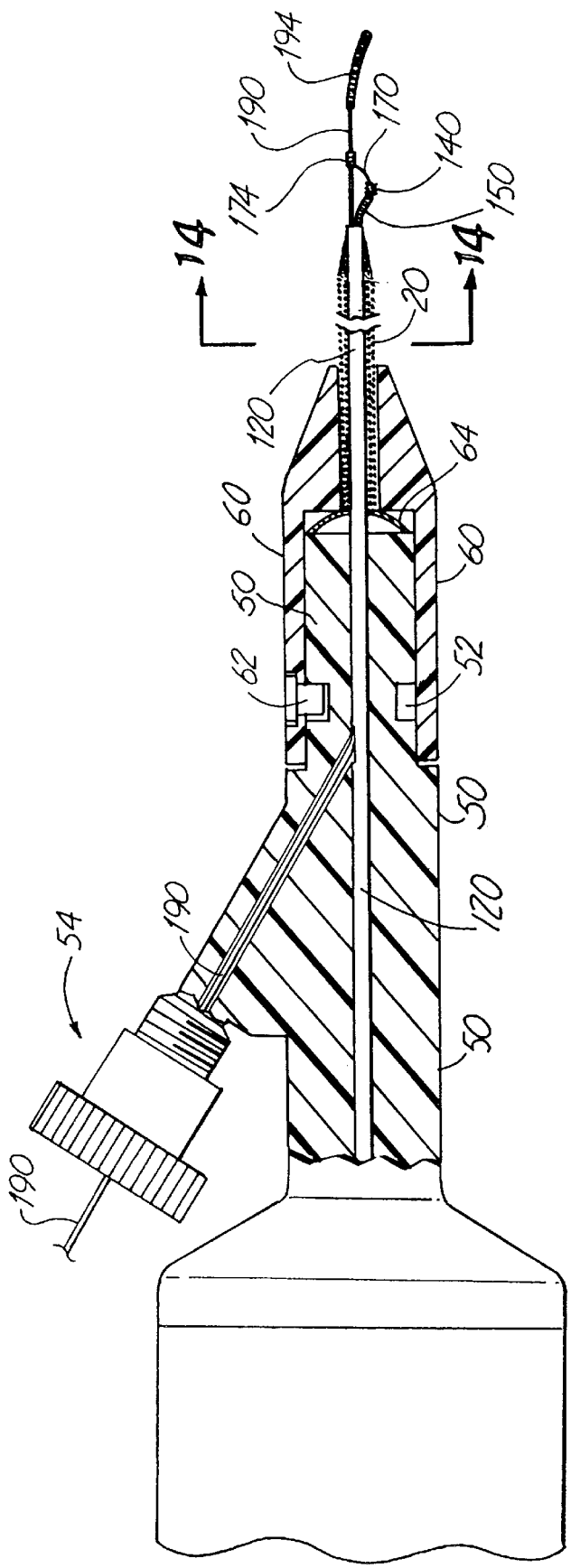
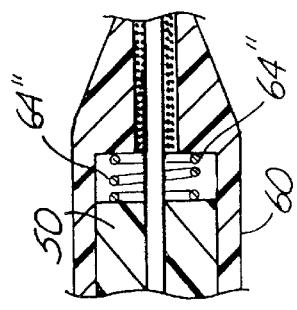
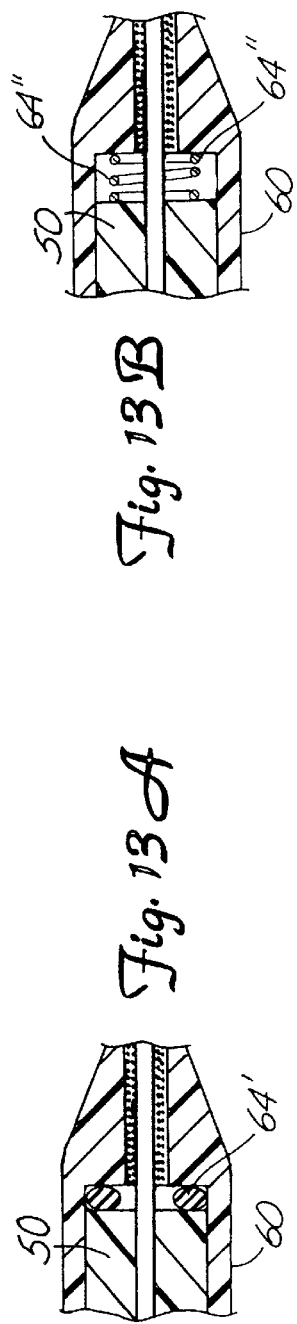
Fig. 13
Fig. 13A
Fig. 13B

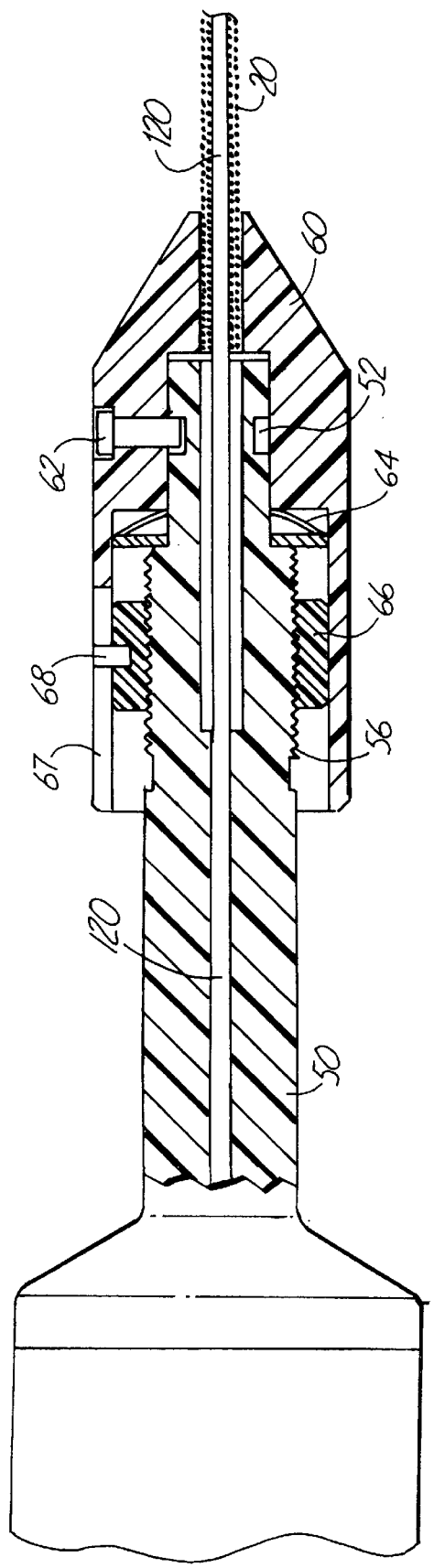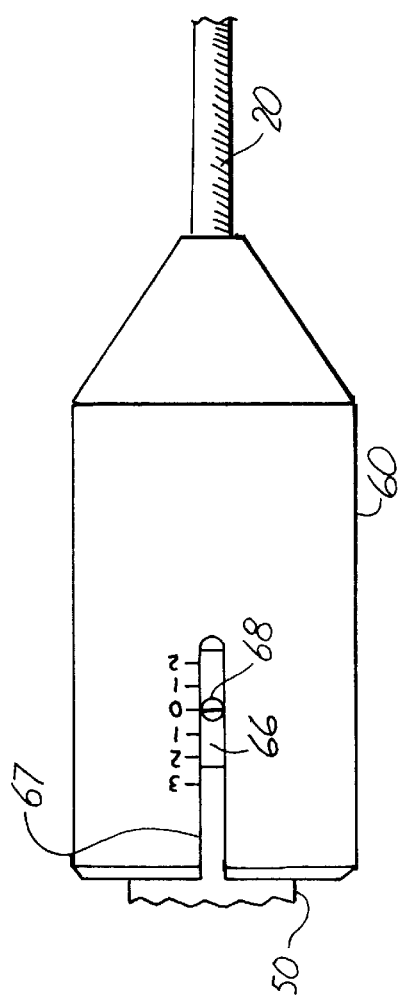
Fig. 18
Fig. 19

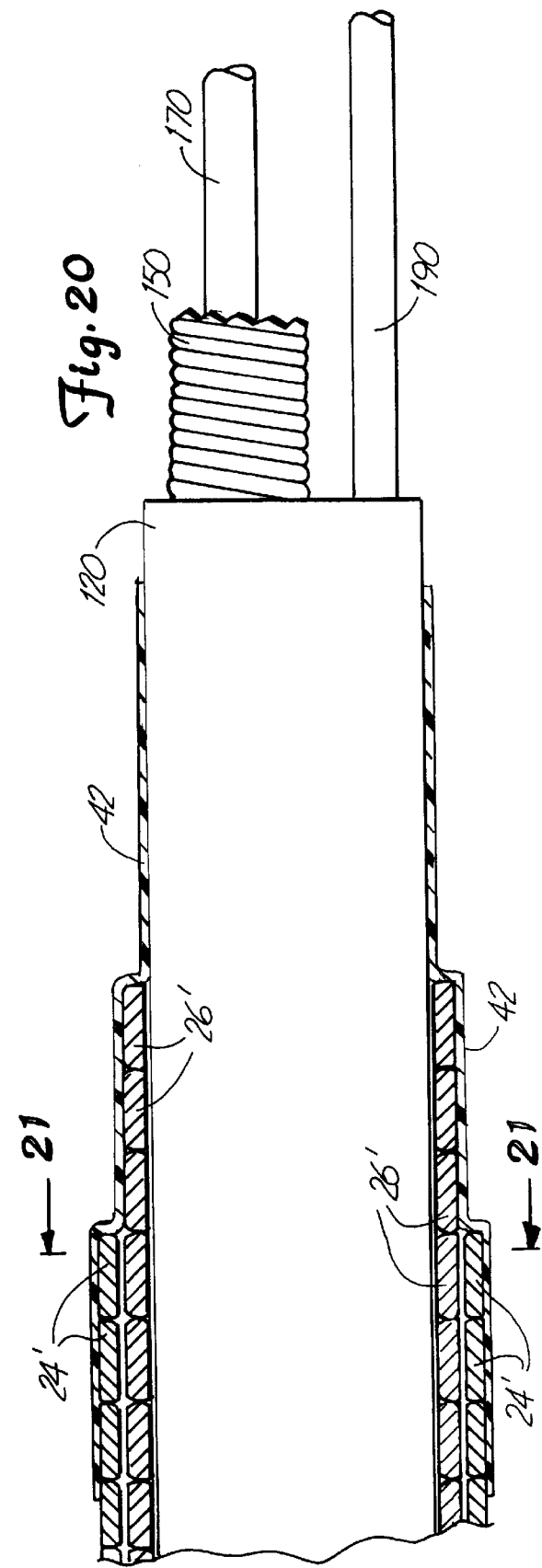
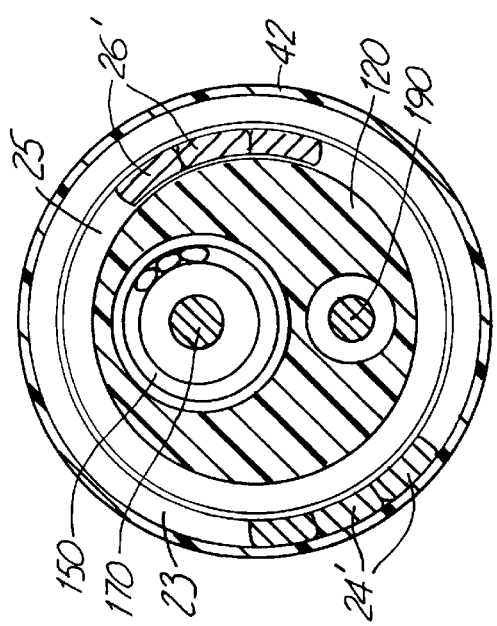

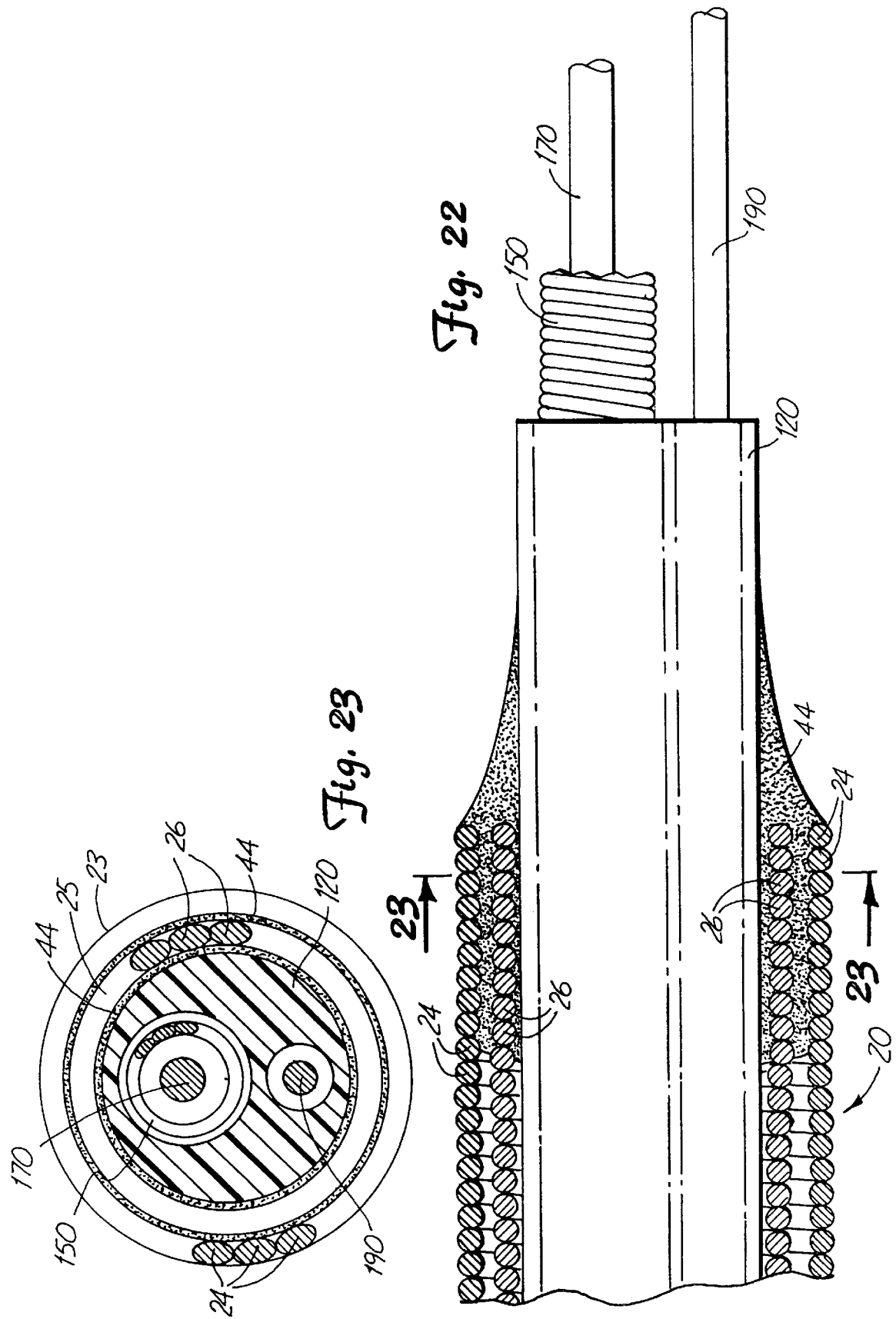

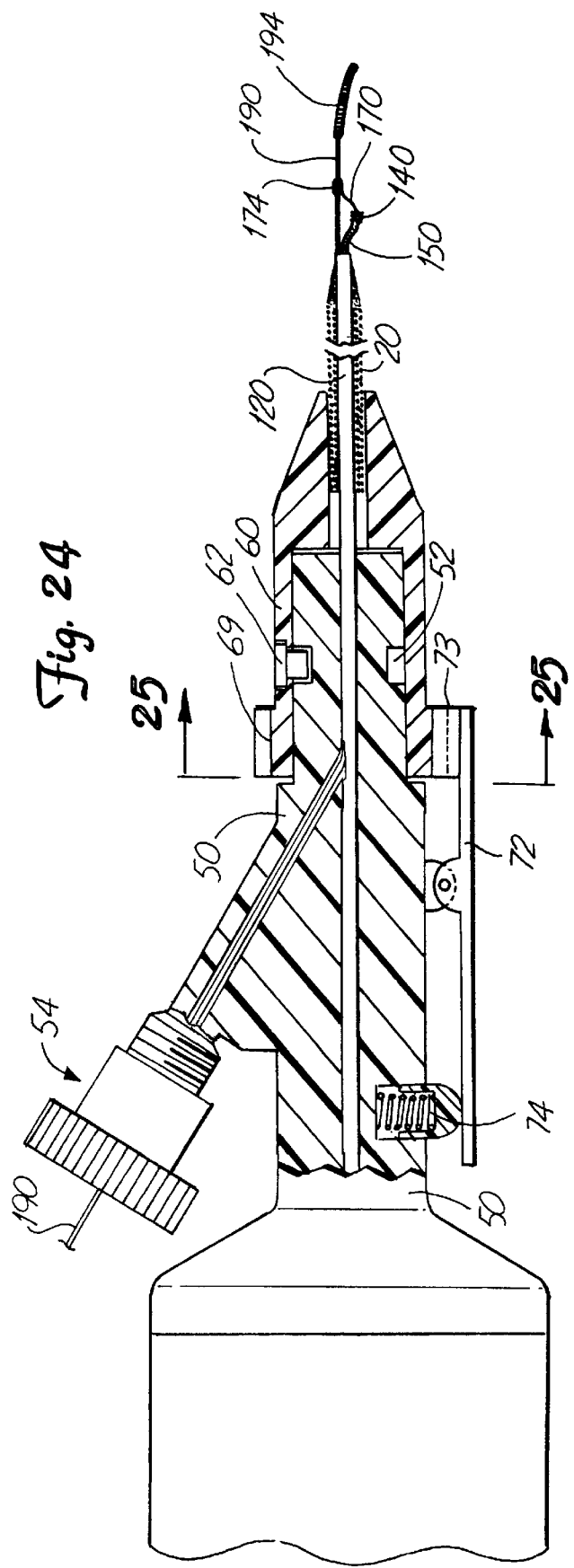
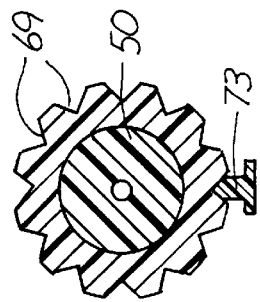
Fig. 24
Fig. 25

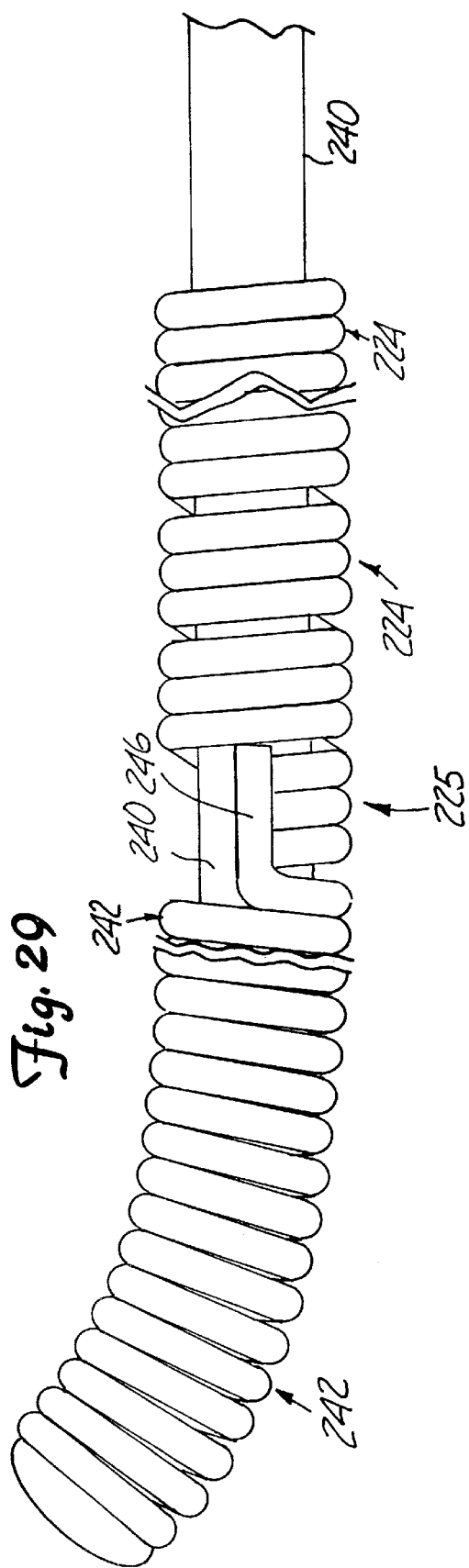
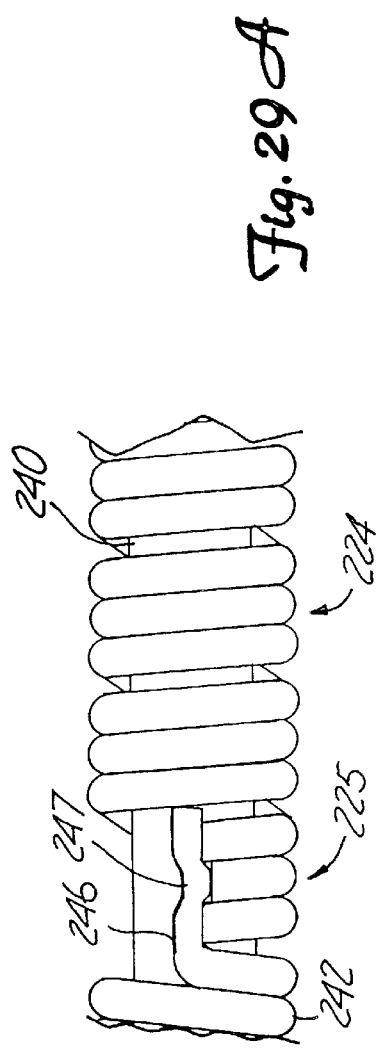
Fig. 29
Fig. 29A

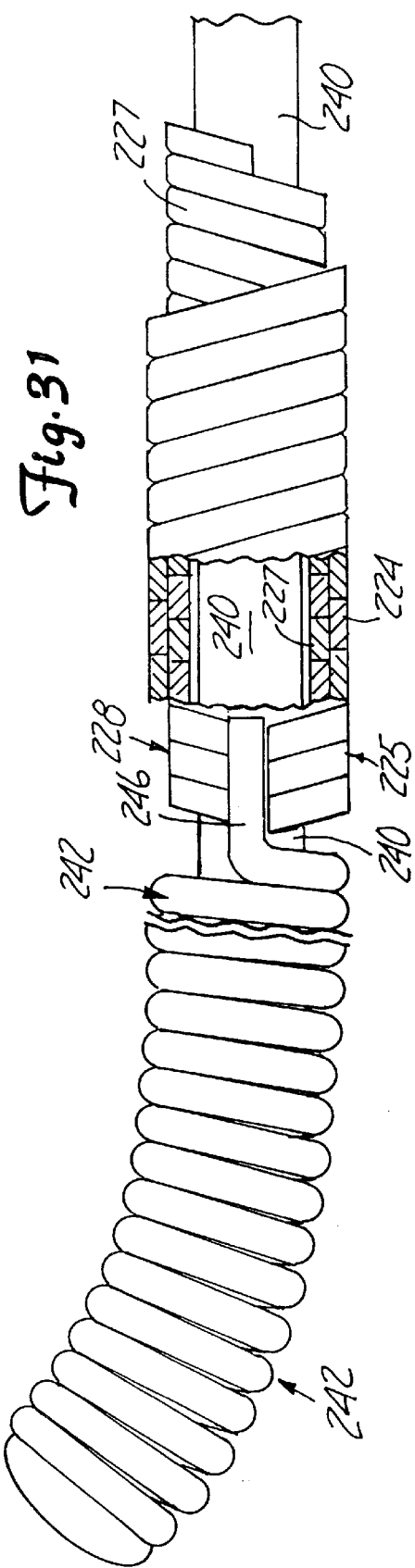
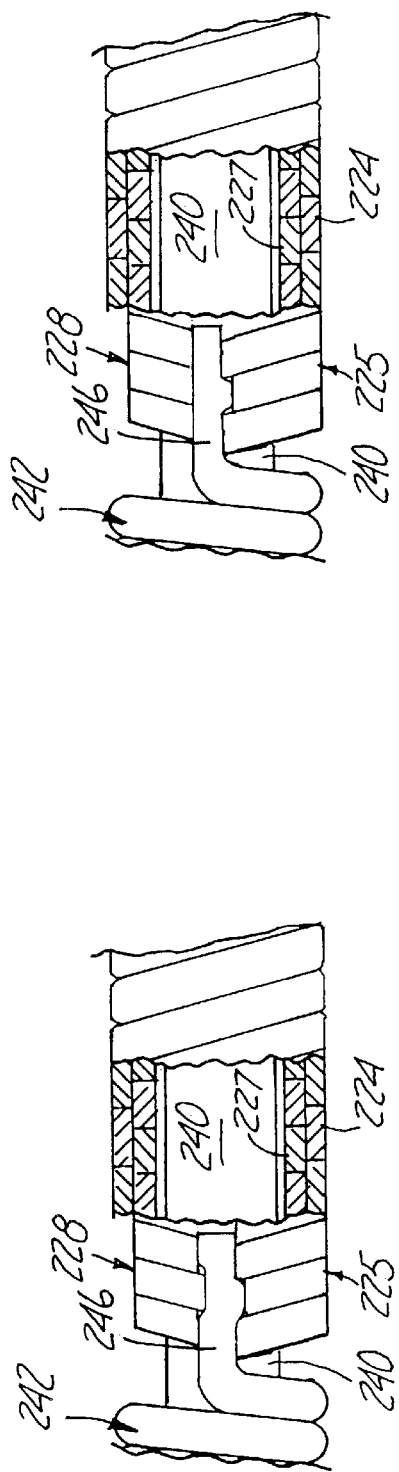

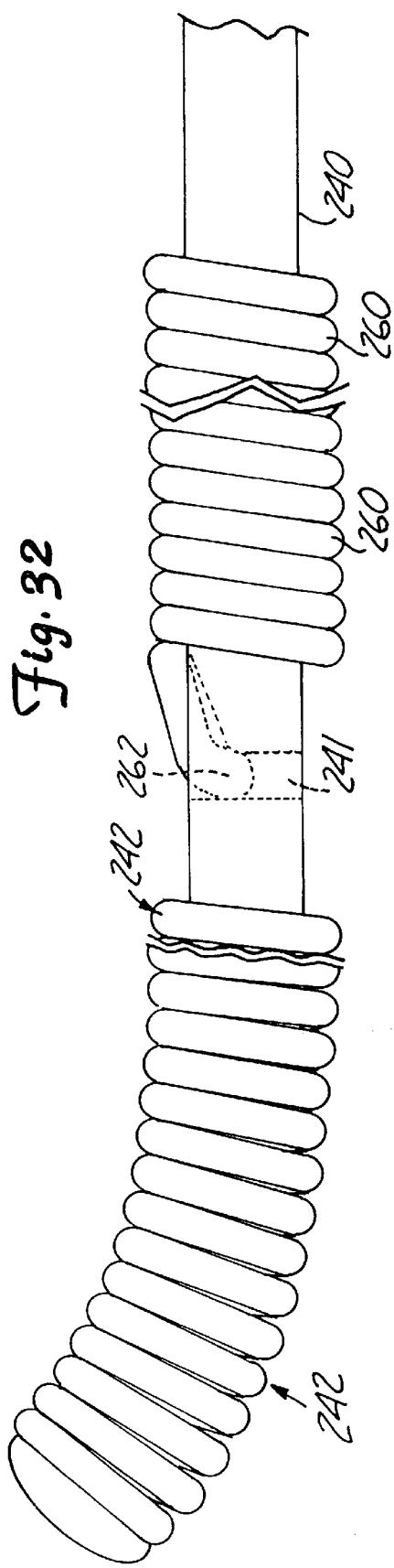
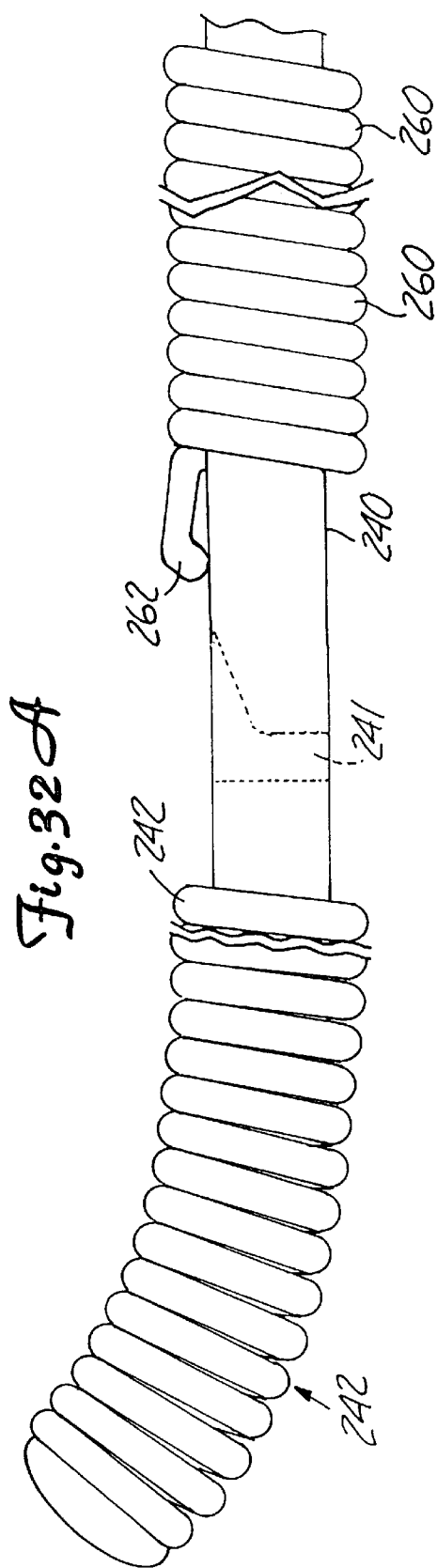

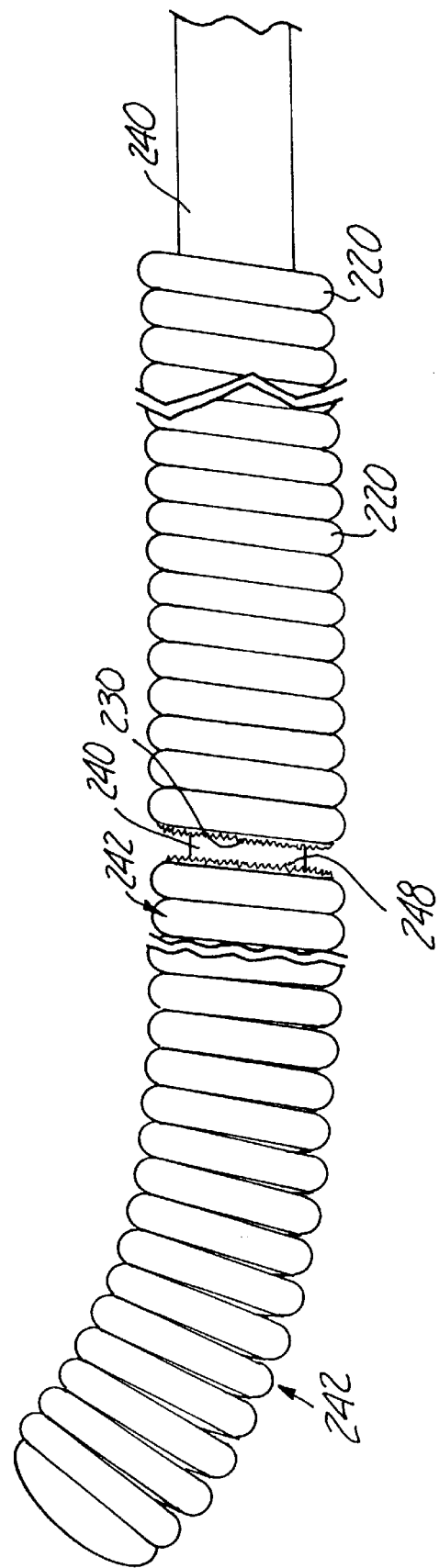

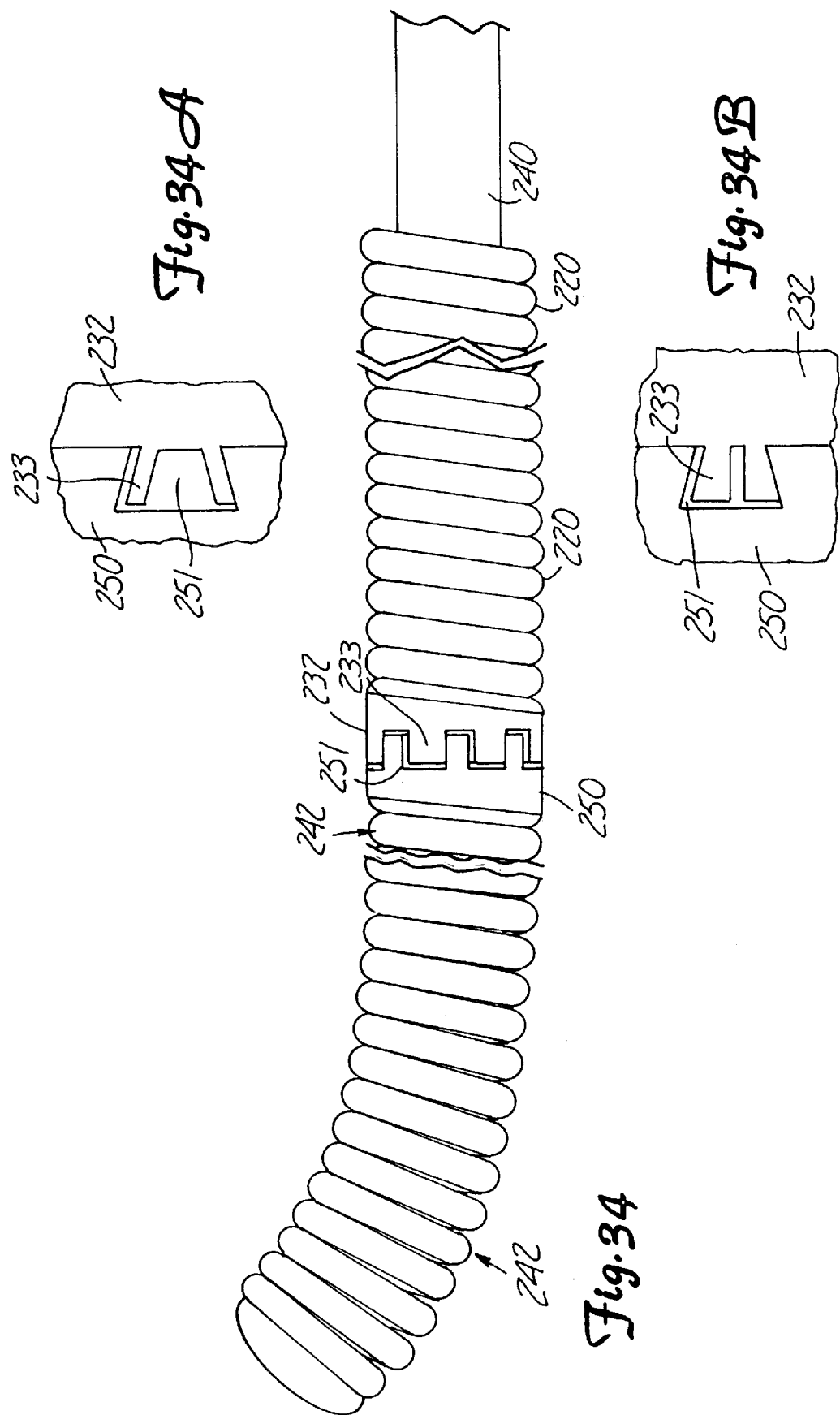

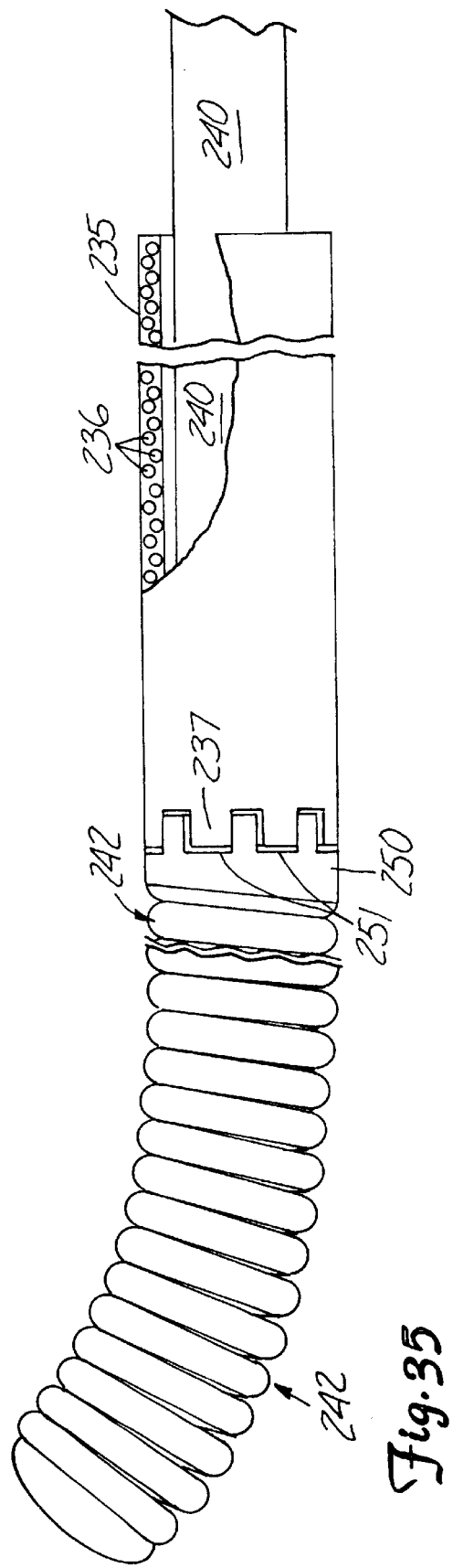

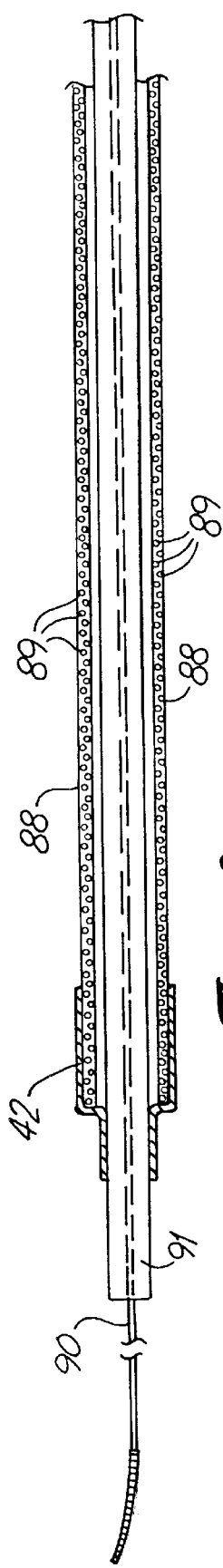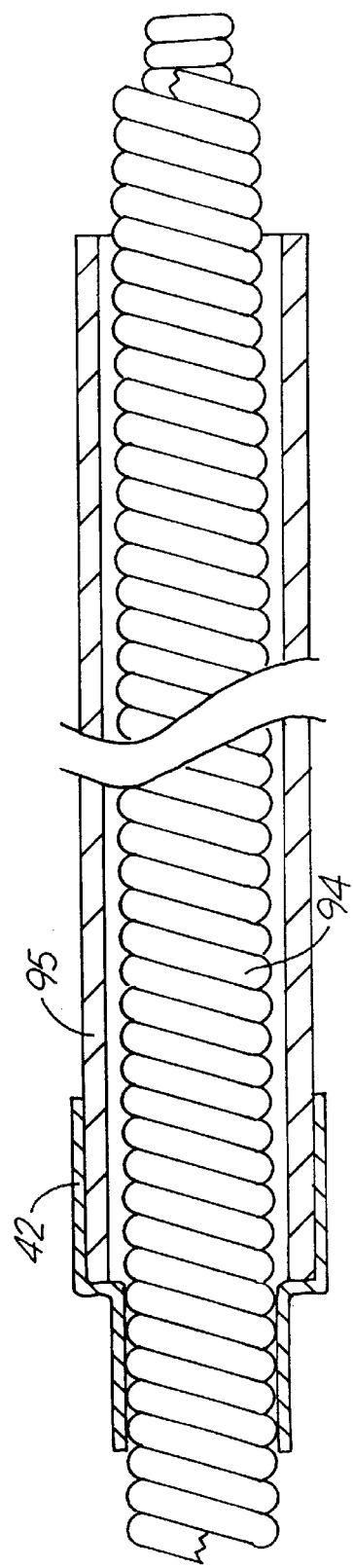

ROTATABLE INTRAVASCULAR APPARATUS

FIELD OF THE INVENTION

The invention relates to medical devices, and more particularly to a medical apparatus incorporating an elongated medical device having a distal end portion, the rotational orientation of which is desired to be controlled.

BACKGROUND OF THE INVENTION

Elongated medical devices such as guide wires, guiding catheters, ultrasonic catheters, atherectomy devices, catheters for radiofrequency (RF) cardiac ablation, etc., are used extensively by interventional cardiologists and interventional radiologists. Elongated medical devices are utilized as well in neuro-surgical, orthopedic, ear-nose-throat, and obstetrical and gynecological procedures, etc. to perform many diagnostic and/or interventional procedures without the need for more traditional surgery. Typically, the elongated medical device is introduced percutaneously, providing access to some remote location within the body, such as, e.g., a coronary artery. In some circumstances, the rotational orientation of the distal end of the medical device is irrelevant, such as with certain ultrasound catheters. In other circumstances, however, the rotational orientation of the distal end of a medical device is very important. For example, catheters used to map the electrical potential of the myocardium (and similar catheters used for cardiac ablation) typically have a distal end portion with a preshaped configuration to facilitate placement of the distal end of the catheter in various positions within the chambers of the heart. Rotational control of such devices is also very important. Shturman has described certain directional rotational atherectomy devices for which control of the rotational orientation of the distal end of the device is important (see, e.g., U.S. Pat. No. 5,360,432).

Common techniques for providing such control of the rotational orientation of a device's distal end have typically relied on the use of wire reinforcement (such as wire braiding) embedded in the device (e.g., in the wall of a catheter). While such reinforcement increases the torque-conveying ability of the device, the efficacy of this technique nevertheless depends on the ability of the device to convey rotation in a 1:1 ratio from the proximal end to the distal end. That is, after inserting the device to the desired location, in order to achieve the desired rotational position, the physician turns the proximal end of the device, and relies on the device's ability to convey that rotation in a 1:1 ratio to the distal end of the device. Thus, a 90° rotation of the proximal end is intended to result in a 90° rotation of the distal end of the device.

In practice, however, this result is more difficult to accomplish. A physician often may be using a relatively thin, flexible device having a length of up to four or five feet, inserted through a sometimes winding or even tortuous path. As a result, a significant amount of friction can be encountered over the length of the device, and the 90° rotation of the proximal end does not always result in a 90° rotation of the distal end. Rather, a lesser degree of rotation (or no rotation at all) occurs at the distal end, with torque building up through the length of the device. Further rotation of the proximal end is required to overcome the friction, but can result in the distal end "whipping" and over-rotating (i.e., once the distal end begins to rotate, since the coefficient of dynamic friction is less than the coefficient of static friction, the built-up torque is released and the distal end of the device rotates the full amount that the proximal end had been rotated, a degree of rotation greater than what the physician intended).

Thus, while reinforcing braids, etc., improve the torque-conveying abilities of such devices, they rely on the theoretical 1:1 rotation ratio (which is difficult to obtain in actual use), and they are still subject to "whip", thus making it difficult to provide the desired degree of control over the rotational orientation of the distal end of the device.

Reinforcing braids also tend to reduce the lateral flexibility of such elongated medical devices and, thus, the ability to track well (over guide wires, for example) through tortuous vasculature.

SUMMARY OF THE INVENTION

The invention provides a system for gaining significant control over the rotational orientation of the distal end of a flexible, elongated medical device. The invention includes a flexible torquing sheath extending along a substantial length of the elongated medical device, the sheath having proximal and distal ends and an intermediate segment. The distal end of the torquing sheath is secured to the distal portion of the medical device, but not to the intermediate or proximal portions of the medical device, so that rotation of the proximal end of the torquing sheath with respect to the proximal portion of the medical device conveys torque to the distal end of the torquing sheath and, therefore, to the distal portion of the medical device, thereby rotating the distal portion of the medical device. By holding the proximal portion of the medical device and preventing the proximal portion from rotating while the distal portion is rotated by the torquing sheath, a certain amount of torque is built up along the length of the medical device; this torque tends to resist rotation of the distal portion of the medical device, and therefore provides a force which resists or dampens the tendency of the distal portion of the elongated medical device to "whip" when the torquing sheath is rotated.

In a preferred embodiment, the invention includes a stabilizing handle secured to the proximal portion of the medical device and a rotation grip secured to the proximal end of the torquing sheath. The rotation grip is rotatable with respect to the stabilizing handle for facilitating selective rotation of the proximal end of the torquing sheath with respect to the proximal portion of the medical device, thereby rotating the distal portion of the medical device with respect to the proximal portion of the medical device. The device may include a relative rotation counter indicating the extent of relative rotation of the rotation grip with respect to the stabilizing handle, the extent of such rotation being correlated with corresponding rotation of the distal end of the medical device.

The apparatus of the invention is usable, for example, in connection with a wide variety of devices, including, for example, atherectomy devices and catheters, including guiding catheters and catheters used in radiofrequency (RF) cardiac ablation procedures and catheters used for mapping the electrical potentials of a patient's myocardium.

The apparatus of the invention may also be successfully utilized to temporarily (when needed) increase the rotational control of the distal end of guide wires or guiding catheters.

BRIEF DESCRIPTION OF THE DRAWINGS

FIG. 13 is a broken-away view in partial longitudinal cross-section of the embodiment of FIG. 12;

FIGS. 13A and 13B are broken-away views in partial longitudinal cross-section of alternate embodiments of a portion of the handle shown in FIG. 13;

FIG. 18 is a broken-away view in partial longitudinal cross-section of another embodiment of the invention;

FIG. 19 is a broken-away view of a portion of the embodiment depicted in FIG. 18;

FIG. 20 is a partial cross-sectional, broken-away view depicting attachment of the distal end of the torquing sheath to the distal end portion of the medical device;

FIG. 21 is a cross-sectional view of FIG. 20, taken along lines 21—21 thereof;

FIG. 22 is a partial cross-sectional, broken-away view of an alternative method of attachment of the distal end of the torquing sheath to the distal end portion of the medical device;

FIG. 23 is a cross-sectional view of FIG. 22, taken along lines 23—23 thereof;

FIG. 24 is a partial cross-sectional, broken-away view of another embodiment of the invention;

FIG. 25 is a cross-sectional view of FIG. 24, taken along lines 25—25 thereof;

FIG. 29 is a broken-away view similar to FIG. 27, depicting another embodiment of the invention utilizing a torquing sheath having a distal end which is removably engageable with the proximal end of the distal portion of the medical device;

FIG. 29A is a broken-away view similar to FIG. 29, depicting a modified configuration of the distal end of the torquing sheath and the proximal end of the distal portion of the medical device;

FIG. 31 is a broken-away view similar to FIG. 29, depicting another embodiment of the invention utilizing a two-layer torquing sheath having a distal end which is removably engageable with the proximal end of the distal portion of the medical device;

FIGS. 31A and 31B are broken-away views similar to FIG. 31, depicting modified configurations of the distal end of the torquing sheath and the proximal end of the distal portion of the medical device;

FIGS. 32 and 32A are broken-away views similar to FIGS. 29–30, depicting another embodiment of the invention utilizing a torquing sheath having a distal end which is removably engageable with a slot formed in the distal portion of the medical device;

FIG. 33 is a broken-away view similar to FIG. 31, depicting another embodiment of the invention utilizing a torquing sheath having a distal end with a friction interface for removable engagement with a friction interface on the proximal end of the distal portion of the medical device;

FIG. 34 is a broken-away view similar to FIG. 33, depicting another embodiment of the invention utilizing a torquing sheath having a distal end with distally extending protrusions receivable in complementary recesses in the proximal end of the distal portion of the medical device;

FIGS. 34A and 34B are broken-away views of alternate embodiments of the size and shape of the protrusions and recesses of the device depicted in FIG. 34;

FIG. 35 is a broken-away view similar to FIG. 34, depicting another embodiment of the invention utilizing a torquing sheath comprised of a wire braid reinforced tubular sheath;

FIG. 39 is a broken-away view in partial cross-section of another embodiment of the invention utilizing another type of torquing sheath;

FIG. 40 is a broken-away view in partial cross-section of another embodiment of the invention utilizing a torquing sheath disposed inside of the medical device;

BEST MODE FOR CARRYING OUT THE INVENTION

Figure 1:
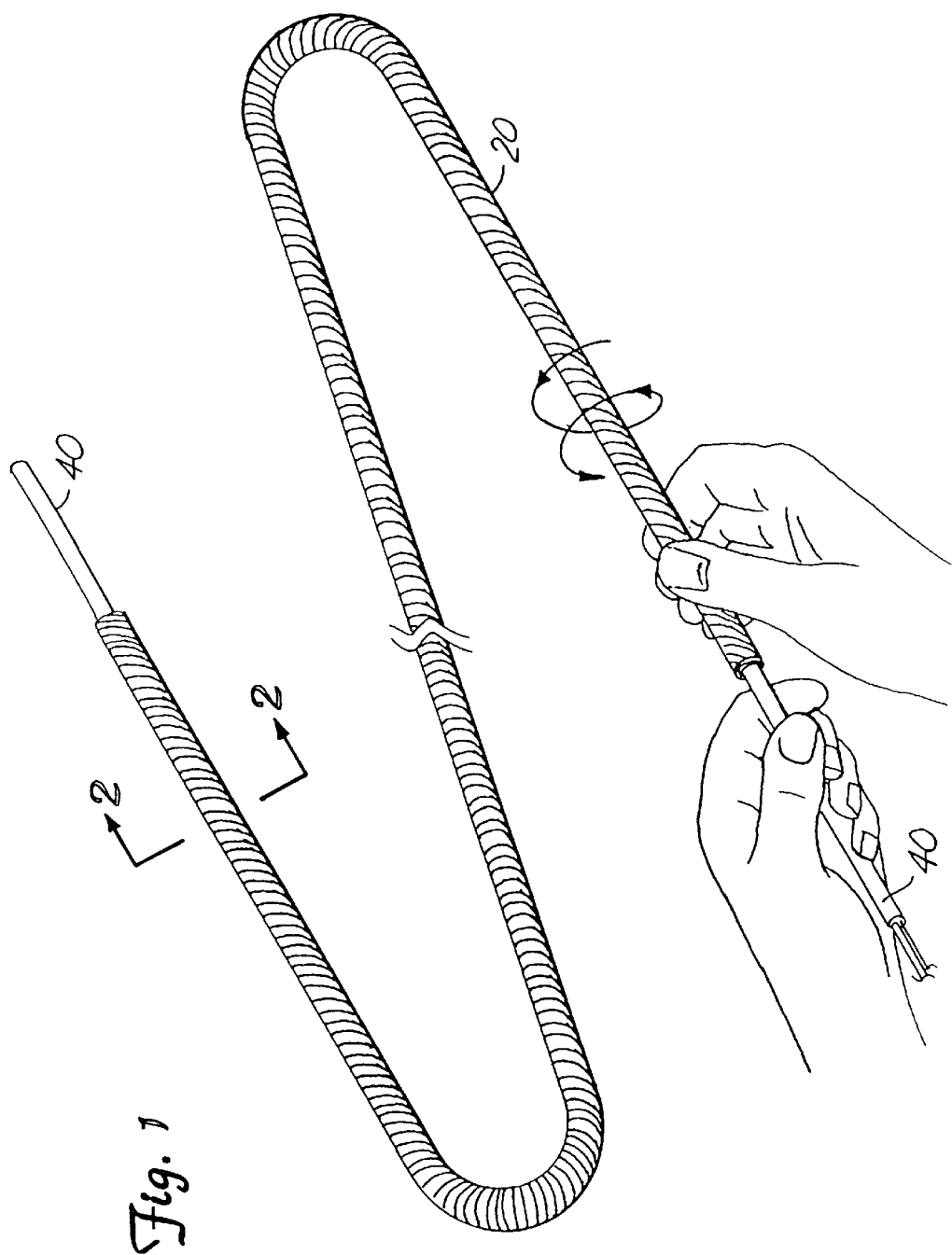
FIG. 1 is a perspective view of a rotatable medical apparatus of the invention.

FIG. 1 depicts in perspective view a rotatable medical apparatus of the invention in a fairly rudimentary form. A torquing sheath 20 is disposed over a catheter or probe (depicted somewhat generically) 40. The distal end of the torquing sheath 20 is secured to the probe 40, but the sheath's intermediate segment and proximal end are not secured to the probe 40, thus permitting relative rotation between the two components except at the distal end of the torquing sheath 20.

Figure 2:
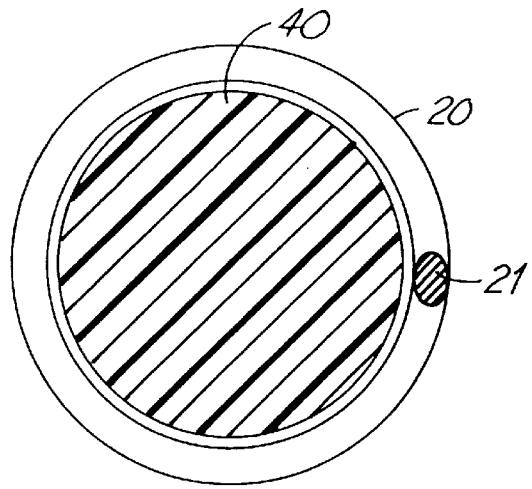
FIG. 2 is a cross-sectional view of FIG. 1, taken along lines 2—2 thereof, depicting a single layer outer torquing sheath.
Figure 3:
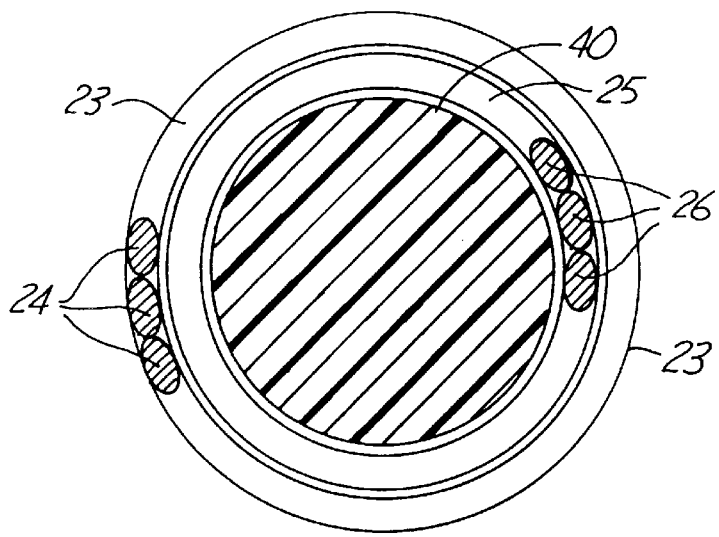
FIG. 3 is a cross-sectional view similar to FIG. 2, depicting a two-layer outer torquing sheath, each layer being tri-filar.
Figure 4:
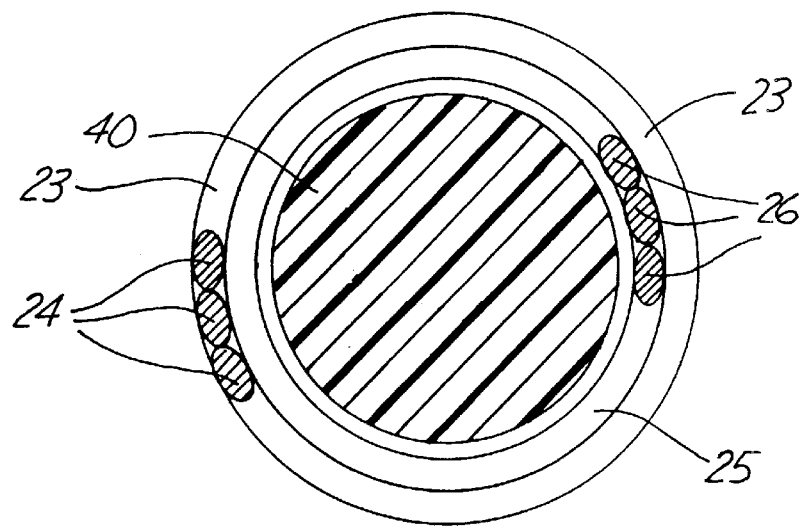
FIG. 4 is a cross-sectional view similar to FIG. 3, depicting the two-layer outer torquing sheath in a moved position.

FIG. 2 depicts the probe 40 generically, showing the torquing sheath 20 as being composed of a single helical wire 21, The wire 21 is wound in a helix with an inner diameter slightly larger than the outer diameter of the probe 40, to permit relative rotation of the sheath 20 with respect to the probe 40. FIGS. 3 and 4 depict a two-layer sheath, the outer layer 23 consisting of three helically wound wire strands 24, and the inner layer 25 consisting of three helically wound wire strands 26, the wire strands 26 of the inner layer 25 being wound in the opposite direction as the wire strands 24 of the outer layer 23. FIG. 3 depicts the two-layer torquing sheath in a relaxed position with the outer layer 23 having an internal diameter slightly larger than the outer diameter of the inner layer 25, thus resulting in a slight gap between the two layers. If the proximal end of the torquing sheath is rotated in the direction that the inner layer 25 is wound (i.e., viewed proximally to distally), the inner layer 25 will tend to expand in diameter, and the outer layer will tend to contract in diameter, thus resulting in the configuration shown in FIG. 4 (i.e., the slight space between the two layers has been eliminated). In this configuration, the sheath conveys torque quite effectively (in the direction that the inner layer 25 is wound) from its proximal end to its distal end.

Figure 5:
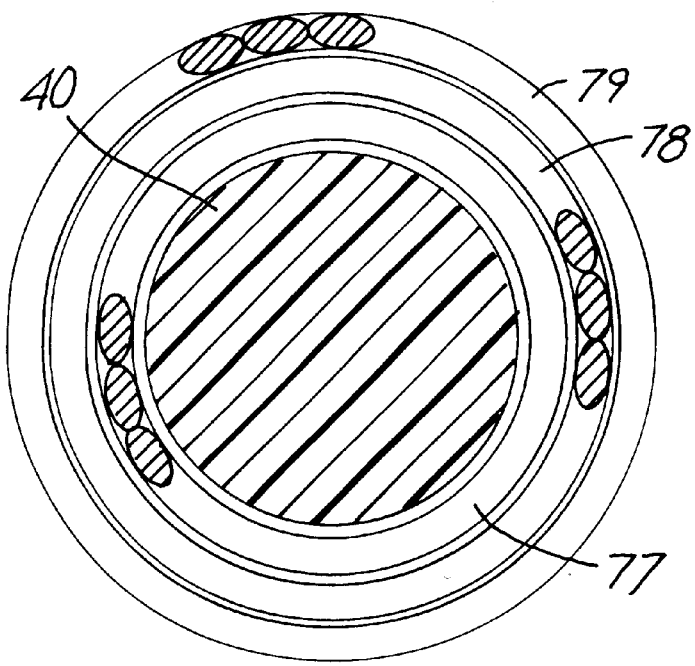
FIG. 5 is a cross-sectional view similar to FIG. 3, depicting a three-layer outer torquing sheath.
Figure 6:
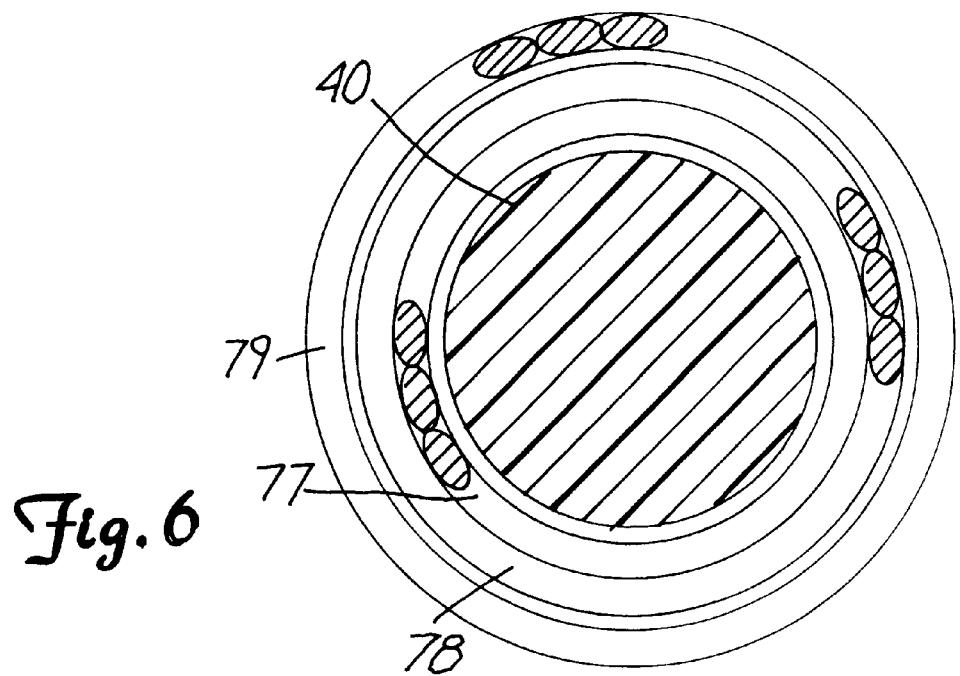
FIG. 6 is a cross-sectional view similar to FIG. 5, depicting the three-layer outer torquing sheath in a moved position.
Figure 7:
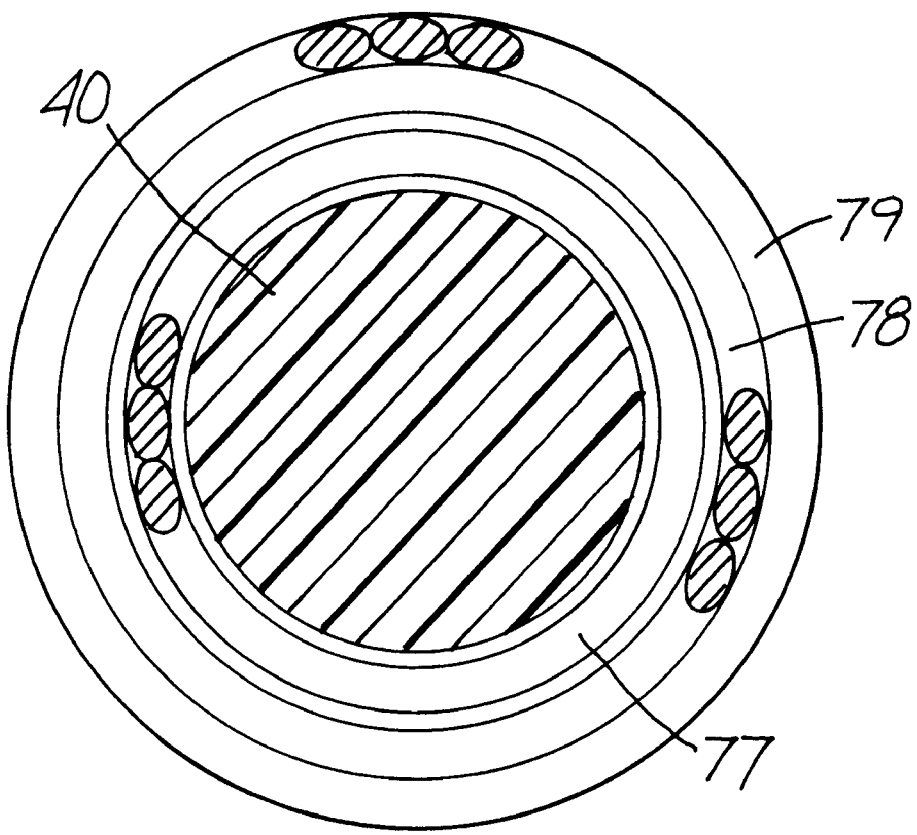
FIG. 7 is a cross-sectional view similar to FIG. 6, depicting the three-layer outer torquing sheath in an opposite moved position.

FIGS. 5–7 are cross-sectional views similar to FIGS. 2–4, but depicting a three-layer torquing sheath and illustrating relative movement of the three layers of the torquing sheath in use. Each of the layers is tri-filar (i.e., made from three helically wound wires). The inner and outer layers 77 and 79 preferably are wound in the same direction, and the middle layer 78 preferably is wound in the opposite direction. FIG. 5 depicts the three-layer torquing sheath in a relaxed position, with each of the layers slightly spaced from the other. When the proximal end of the torquing sheath is rotated in the same direction that the inner layer 77 is wound (i.e., viewed proximally to distally), the inner and outer layers 77 and 79 will tend to expand in diameter, and the middle layer 78 will tend to contract in diameter, thus resulting in the configuration shown in FIG. 6 (i.e., the slight space between the inner and middle layers 77 and 78 has been eliminated). When the proximal end of the torquing sheath is rotated in the opposite direction, the inner and outer layers 77 and 79 will tend to contract in diameter, and the middle layer 78 will tend to expand in diameter, thus resulting in the configuration shown in FIG. 7 (i.e., the slight space between the middle and outer layers 78 and 79 has been eliminated). In either of these configurations (i.e., FIG. 6 or 7), the engagement of the layers of the sheath with one another causes the sheath to convey torque quite effectively (in FIG. 6, in the direction that the inner layer 77 is wound, and in FIG. 7, in the direction that the middle layer 78 is wound) from its proximal end to its distal end.

Figure 8:
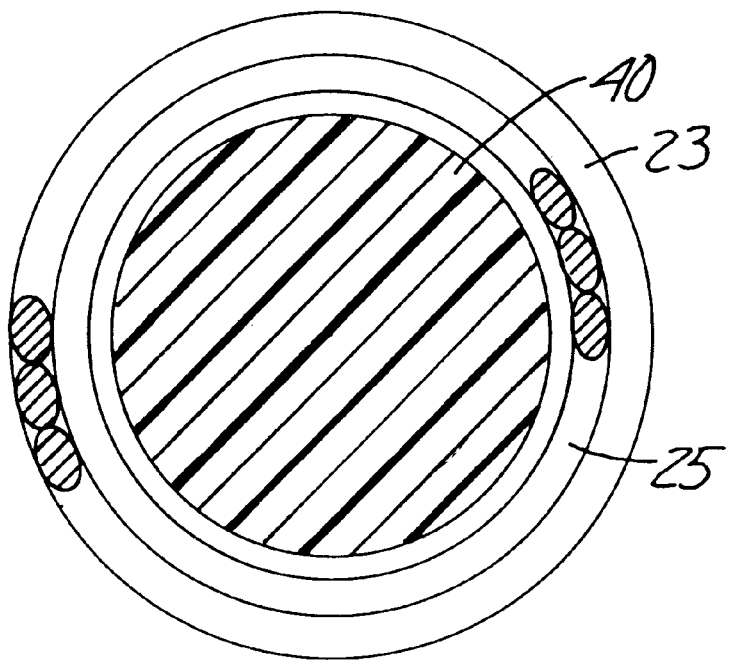
FIG. 8 is a cross-sectional view similar to FIG. 3, depicting a two-layer interference fit outer torquing sheath.
Figure 9:
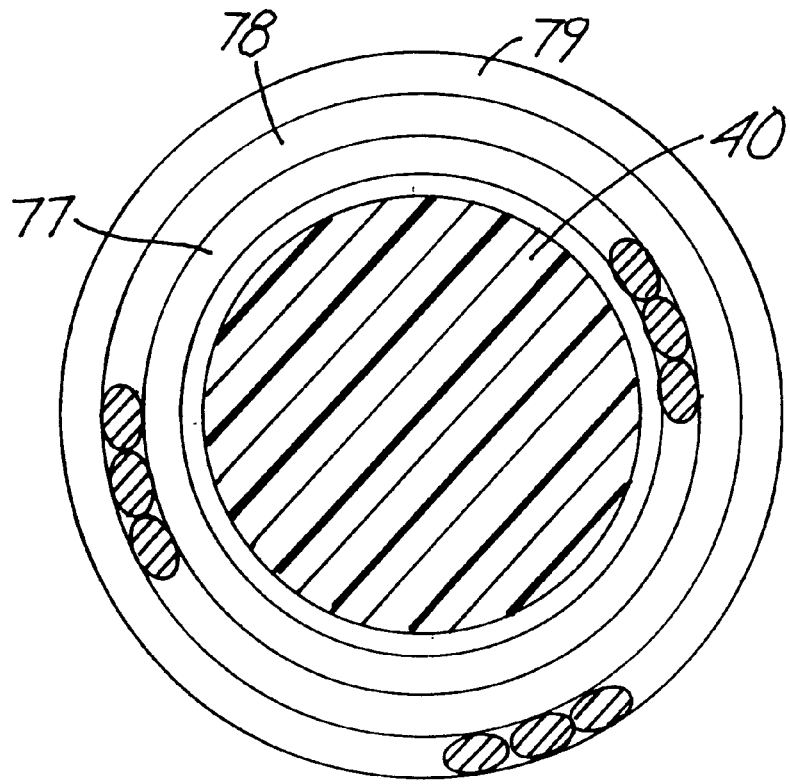
FIG. 9 is a cross-sectional view similar to FIG. 8, depicting a three-layer interference fit outer torquing sheath.

If desired, the torquing sheath can be made from two helically wound wire layers having an interference fit, as shown in FIG. 8. Preferably the two wire layers are wound helically in opposite directions, with the normal, at-rest outer diameter of the inner layer 25 being slightly larger than the normal, at-rest inner diameter of the outer layer 23. Two-layer helically wound cables having an interference fit are described in U.S. Pat. No. 5,165,421 (Fleischhacker). Utilizing an interference fit in a two-layer torquing sheath of the invention allows rotation of the medical device 40 in both directions, though in one direction, much higher torque can be conveyed than in the other direction. FIG. 9 shows a three layer torquing sheath assembled with an interference fit between each of the layers. The inner and outer layers, 77 and 79 respectively, are wound in the same direction, and the middle layer 78, is wound in the opposite direction as the other two layers. This embodiment provides high torque conveyance ability in both rotational directions.

As indicated above, FIGS. 1–9 depict the medical device somewhat generically as a probe 40. The invention can be utilized with a wide variety of elongated, flexible medical devices, however. FIGS. 10–26 illustrate one specific application, it being understood that the principles depicted in these drawings could be applied in connection with other types of medical devices.

Figure 10:
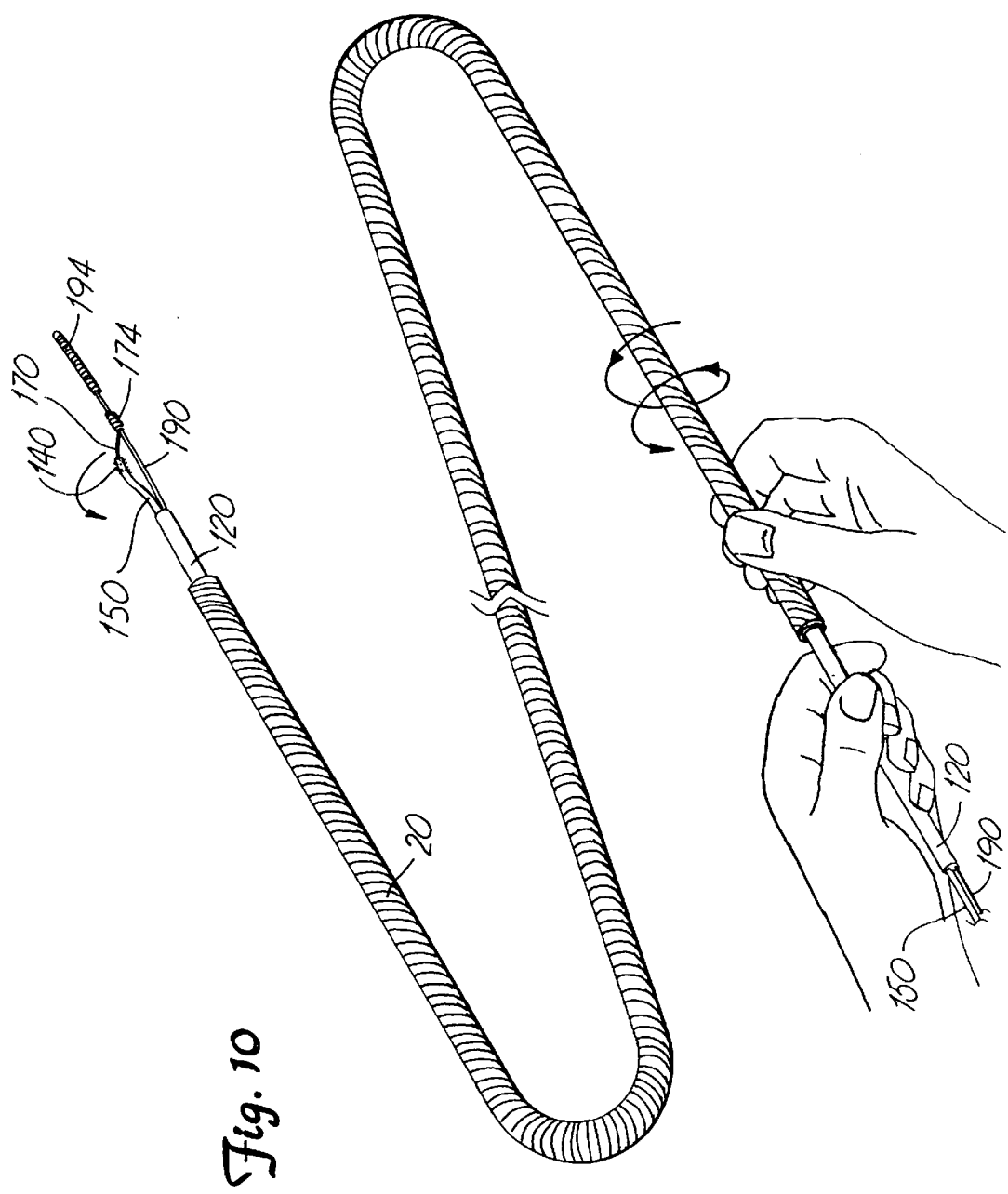
FIG. 10 is a perspective view of a rotatable medical apparatus of the invention utilized in connection with a directional rotational atherectomy device.

In FIG. 10 the medical device is a directional rotational atherectomy device of the type described in U.S. Pat. No. 5,360,432 (Shturman), which is incorporated herein by reference. This device utilizes a dual lumen catheter 120. A conventional guide wire 190 having a conventional helically wound distal tip portion 194 is disposed in one of the lumens, and a flexible drive shaft 150 is disposed over and is rotatable over a positioning wire 170 in the other lumen. The positioning wire 170 is slidably secured at its distal end 174 to the guide wire 190 so that the positioning wire 170 can be moved proximally and distally with respect to the guide wire 190. The positioning wire 170 includes a distal positioning segment having a predetermined shape. The drive shaft 150 includes a segment near its distal end which is coated with an abrasive material to define an abrasive segment 140 of the drive shaft 150. When the drive shaft's abrasive segment 140 is positioned along the predetermined curved shape of the positioning wire's positioning segment, the positioning segment positions the abrasive segment 140 of the drive shaft 150 laterally away from the guide wire 190, thus giving control over the lateral position of the abrasive segment 140 within the artery. The device therefore allows selective removal of tissue from one side of an artery, permitting selective treatment of eccentric stenotic lesions.

The torquing sheath 20 of the present invention provides rotational control over the rotational orientation of the distal end of the catheter 120, and, therefore over the rotational orientation of the abrasive segment 140 of the drive shaft 150. This permits the physician to rotationally align the abrasive segment with the stenotic tissue desired to be removed from the artery.

Figure 11:
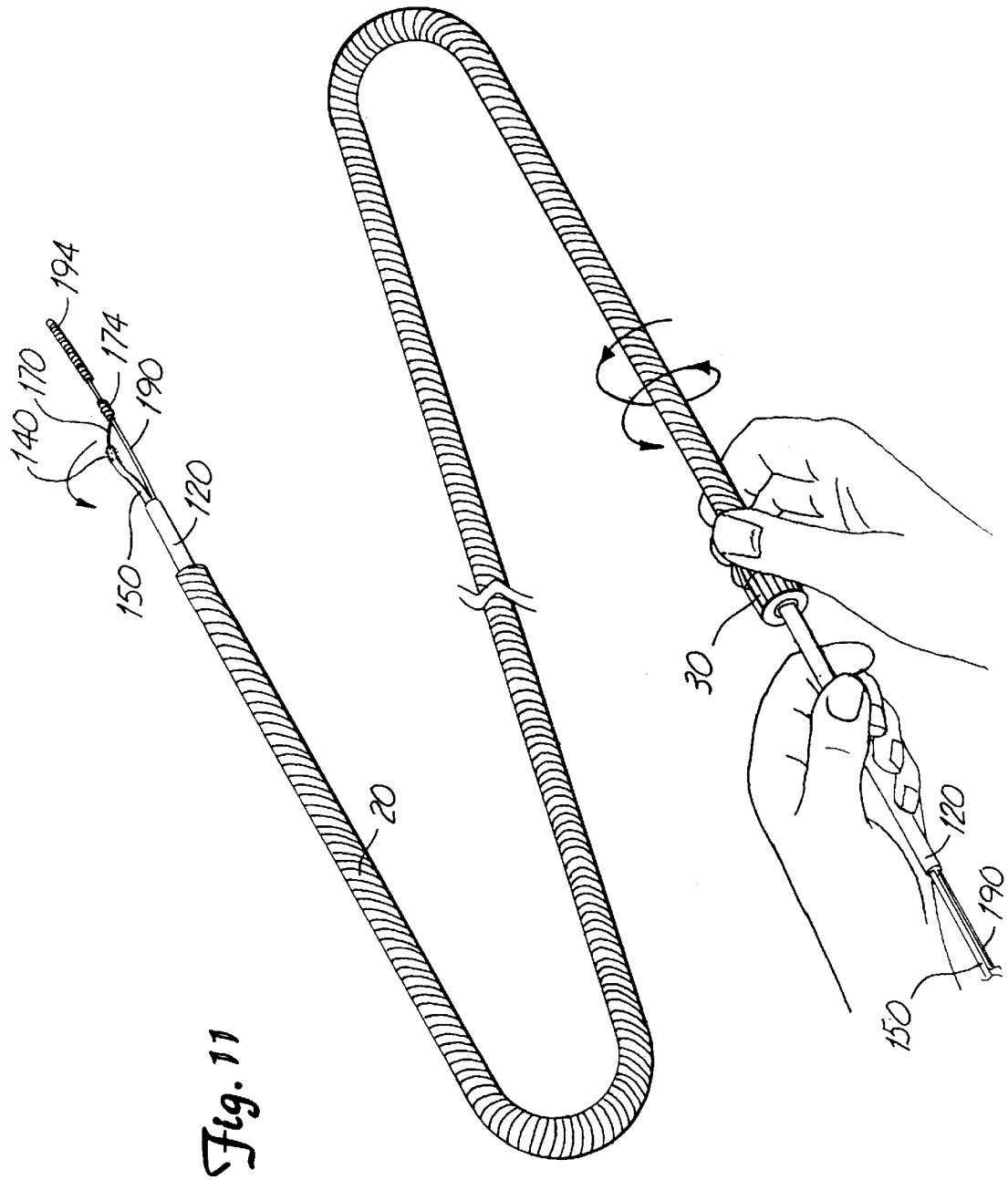
FIG. 11 is a perspective view of an embodiment of the invention similar to FIG. 10 but providing a handle on the proximal end of the torquing sheath.

FIG. 11 illustrates a variation in which the proximal end of the torquing sheath 20 is provided with a simple handle 30 for facilitating manual manipulation of the torquing sheath 20.

Figure 12:
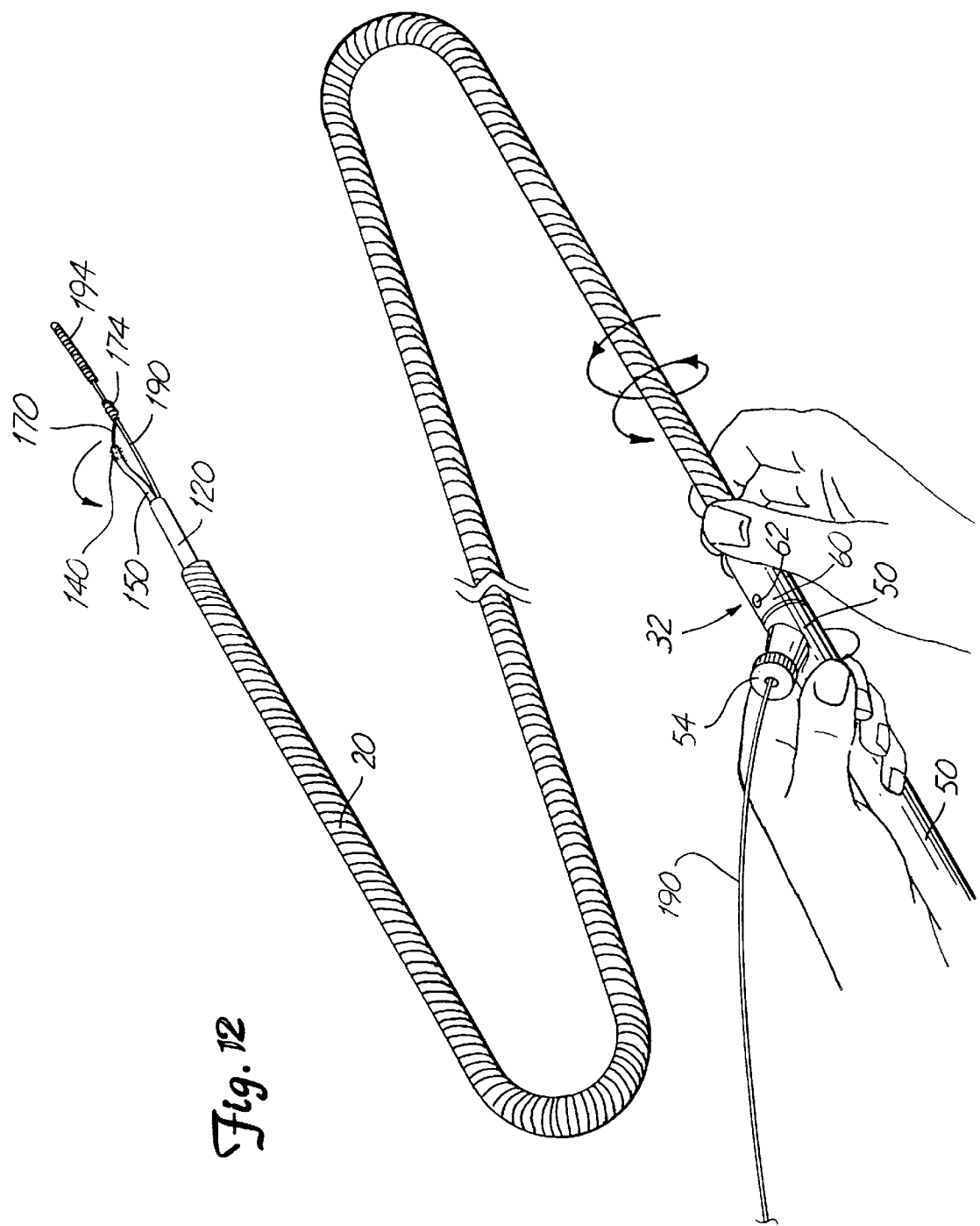
FIG. 12 is a perspective view of another embodiment of the invention similar to FIG. 11 but providing another type of handle at the proximal ends of the torquing sheath and the rotatable medical apparatus.

FIGS. 12–13 illustrate another handle, designated generally as 32, facilitating the manual rotation of the torquing sheath 20 with respect to the catheter 120. The device includes a stabilizing handle 50 secured to the proximal portion of the catheter 120, and a rotation grip 60 secured to the proximal end of the torquing sheath 20. The rotation grip 60 is rotatable with respect to the stabilizing handle 50 to permit for facilitating selective rotation of the proximal end of the torquing sheath 20 with respect to the proximal portion of the catheter 120, thereby rotating the distal portion of the catheter 120 with respect to the proximal portion of the catheter 120.

The stabilizing handle 50, shown in partial cross-section in FIG. 13, includes a central lumen in which the proximal end of the catheter 120 is received and secured. A side port 54 may be provided through which the guide wire 190 extends and may be manipulated. The rotation grip 60 is secured to the proximal end of the torquing sheath 20, and is rotatable with respect to the stabilizing handle 50. A mechanical linkage is provided to prevent relative longitudinal movement of the stabilizing handle 50 with respect to the rotation grip 60. Any type of suitable linkage may be employed. In the embodiment shown in the drawings, a pin 62 carried by the rotation grip 60 extends radially inwardly into a circumferential groove 52 formed in the stabilizing handle 50. This linkage permits relative rotation of the rotation grip 60 with respect to the stabilizing handle 50, while linking the two pieces together to prevent relative longitudinal movement of one with respect to the other.

Desirably the stabilizing handle 50 and rotation grip 60 are so configured and arranged as to inhibit free rotational movement of the two elements relative to one another-not to the point of inhibiting convenient manipulation of the device, but enough inhibition to exceed the torque forces built up in the catheter 120, so that the stabilizing handle 50 and rotation grip 60 will not rotate with respect to one another unless manually manipulated by the physician. Such inhibition may be provided, e.g., by a spring interposed between a surface of the rotation grip and a surface of the stabilizing handle. In the embodiment illustrated in FIG. 13, this inhibition is provided by a generally concave spring 64 (i.e., a concave disk-shaped spring) interposed under sufficient pressure between the stabilizing handle 50 and the rotation grip 60 to provide the desired degree of friction between the two elements. FIG. 13A depicts use of a resilient O-ring 64' as a spring, and FIG. 13B depicts use of a traditional coil-type spring 64" to provide the necessary degree of inhibition on rotation of the rotation grip 60 with respect to the stabilizing handle 50. Although the drawings illustrate the springs as acting between abutting end surfaces of the two components, suitable friction may similarly be supplied between any other adjacent surfaces of these components, such as between the outer circumferential surface of the stabilizing handle 50 and the inner circumferential surface of the rotation grip 60. Other suitable means may also be employed to provide the desired degree of inhibition between these two elements (e.g., see the detent mechanism described in relation to FIGS. 24–25 below).

Figure 14:
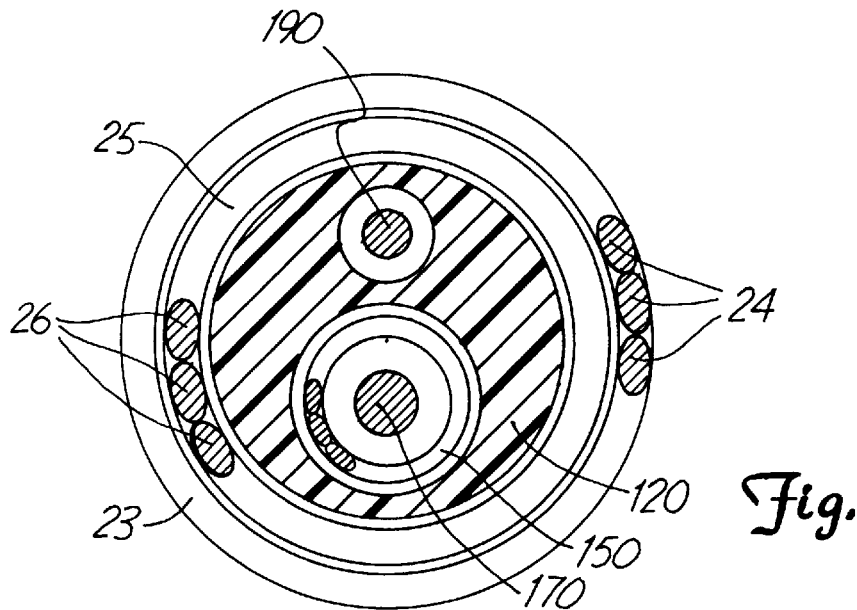
FIG. 14 is a cross-sectional view of FIG. 13, taken along lines 14—14 thereof.
Figure 15:
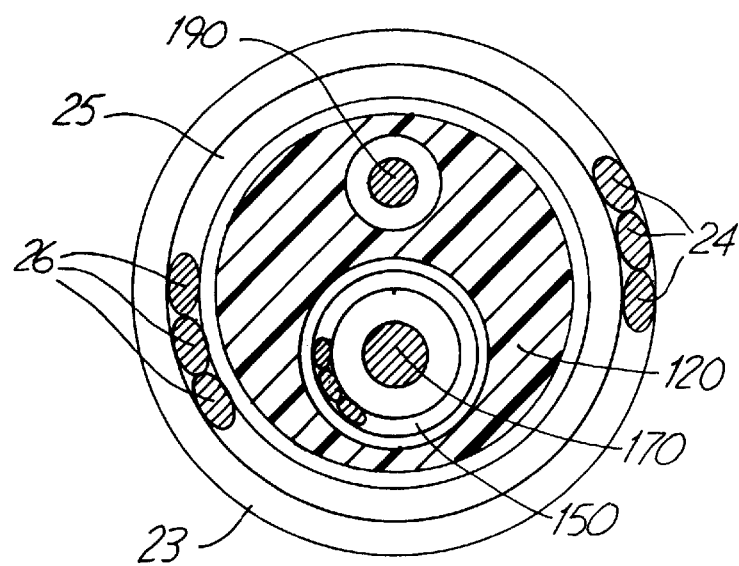
FIG. 15 is a cross-sectional view similar to FIG. 14, depicting the two-layer outer torquing sheath in a moved position.

FIG. 14 is a cross-sectional view of FIG. 13, illustrating a two-layer torquing sheath, with both the inner layer 25 and outer layer 23 in a relaxed position. The outer layer 23 consists of three helically wound wire strands 24, and the inner layer 25 consists of three helically wound wire strands 26, the wire strands 26 of the inner layer 25 being wound in the opposite direction as the wire strands 24 of the outer layer 23. In the relaxed position, shown in FIG. 14, the internal diameter of the outer layer 23 is slightly larger than the outer diameter of the inner layer 25, thus resulting in a slight gap between the two layers. If the proximal end of the torquing sheath is rotated in the direction that the inner layer 25 is wound (i.e., viewed proximally to distally), the inner layer 25 will tend to expand in diameter, and the outer layer will tend to contract in diameter, thus resulting in the configuration shown in FIG. 15 (i.e., the slight space between the two layers has been eliminated). In this configuration, the torquing sheath conveys torque quite effectively (in the direction that the inner layer 25 is wound) from its proximal end to its distal end, thus allowing one to quite effectively control the rotational orientation of both the distal end of the catheter 120 and the distal end of the directional rotational atherectomy device of the type described above.

Figure 16:
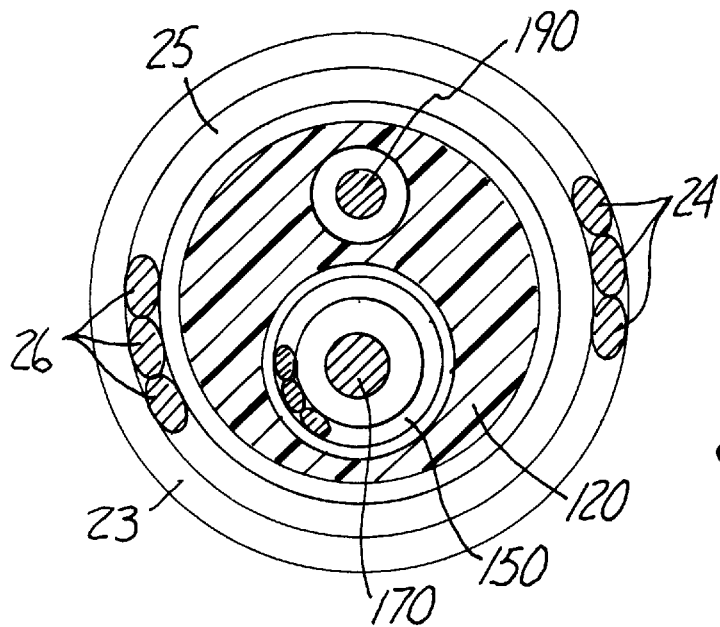
FIG. 16 is a cross-sectional view similar to FIG. 14, depicting a two-layer interference fit outer torquing sheath.
Figure 17:
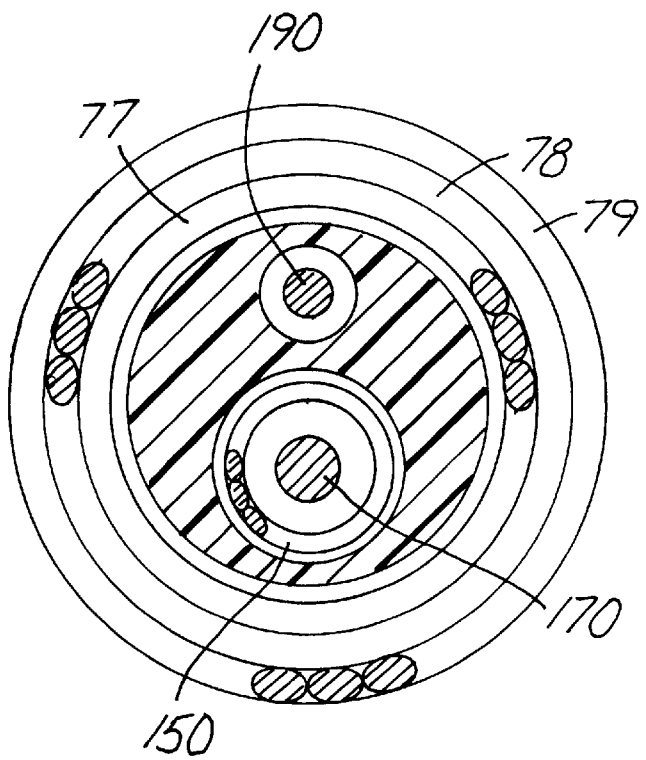
FIG. 17 is a cross-sectional view similar to FIG. 14, depicting a three-layer interference fit outer torquing sheath.

If desired, the directional rotational atherectomy device depicted in FIGS. 12–13 can be constructed with a torquing sheath having two or three layers in interference fit, as described above in connection with FIGS. 8–9. FIG. 16 depicts a cross-sectional view of such a device with a two layer interference fit torquing sheath, and FIG. 17 depicts a cross-sectional view of such a device with a three layer interference fit torquing sheath.

FIGS. 18–19 depict an additional feature which may be incorporated into the rotation grip 60. In this embodiment, the rotation grip 60 includes a relative rotation indicator indicating the extent of relative rotation of the rotation grip 60 with respect to the stabilizing handle 50. Provision of a relative rotation indicator can be accomplished in any of a number of suitable ways. FIGS. 18–19 depict one such arrangement. The relative rotation indicator includes an internally threaded collar 66 disposed within the rotation grip 60. The collar 66 is received over complementary external threads 56 formed in the stabilizing handle 50. The collar 66 carries a radially outwardly extending pin 68 which is received in a longitudinal slot 67 formed in the rotation grip 60. As the rotation grip 60 is rotated with respect to the stabilizing handle 50, the pin 68 causes the collar 66 to rotate along with the rotation grip 60. Thus, the collar 66 moves longitudinally with respect to the rotation grip 60 along the threads 56 of the stabilizing handle 50, and the longitudinal location of the pin 68 in the slot 67 indicates the extent of relative longitudinal movement. Thus, the longitudinal position of the pin 68 indicates the degree of relative rotation of the rotation grip 60 with respect to the stabilizing handle 50. Visible markings, as shown in FIG. 19, may be provided on the rotation grip 60 along the longitudinal slot 67 to give a quantifiable indication of the extent of relative rotation of the rotation grip 60 with respect to the stabilizing handle 50.

FIGS. 20–21 illustrate in greater detail one embodiment of how the distal end of the torquing sheath 20 may be secured to the medical device. In these drawings, the medical device is depicted as being the directional rotational atherectomy device of the type described above-the components of the device depicted in FIGS. 20–21 include the dual lumen catheter 120, the guide wire 190, the drive shaft 150, and the positioning wire 170. In this embodiment, the torquing sheath is made from two layers of generally rectangular wire. As is shown in FIG. 21, preferably each layer is tri-filar (i.e., each includes three strands of the helically wound wire), the wires 24' of the outer layer 23 being wound in a direction opposite that of the wires 26' of the inner layer 25. A short section of a heat shrinkable tube 42 is utilized to secure the wire turns 26' and 24' of the distal end portions of both the inner and outer layers of the torquing sheath to the distal end portion of the catheter 120. The heat shrinkable tubing may be made from any suitable material, such as polytetrafluoroethylene.

FIGS. 22–23 illustrate an alternate embodiment of how the distal end of the torquing sheath 20 may be secured to the medical device. In these drawings, the distal end of the torquing sheath is secured to the distal end portion of the catheter 120 by a suitable adhesive 44. The adhesive also serves to secure the wire turns 24 and 26 of the outer and inner layers 23 and 25 to one another at the distal end of the torquing sheath, and it provides a smooth transition in diameter from the catheter 120 to the slightly larger diameter of the torquing sheath. Preferably both the catheter 120 and the wire from which the torquing sheath is constructed include a lubricous coating, such as polytetrafluoroethylene. Preferably the catheter 120 is made from a lubricous material or is coated with a lubricous material such as polytetrafluoroethylene. Preferably the wire from which the torquing sheath 20 is constructed also includes a lubricous coating of a material such as polytetrafluoroethylene. As a result, other methods of attachment of the distal end of the torquing sheath 20 to the distal end portion of the medical device (catheter 120) may be utilized, e.g., welding (including radiofrequency or ultrasonic welding).

FIGS. 24 and 25 depict a detent mechanism for controlling relative rotation of the rotation grip 60 with respect to the stabilizing handle 50. The detent mechanism comprises a series of notches 69 formed in the rotation grip 60, and a lever 72 pivotally mounted to the stabilizing handle 50. The lever has a tip portion 73 that is engagable with the notches 69 in the rotation grip 60. The lever is biased by a spring 74 so that the tip portion 73 is normally urged into engagement with the notches 69. When the tip portion 73 is engaged with the notches 69, the mechanism substantially prevents relative rotation of the rotation grip 60 with respect to the stabilizing handle 50. When the physician desires to cause such relative rotation, rotation of the rotation grip will result in a camming action urging the tip portion 73 outwardly, overcoming the spring 74 which is biasing the tip portion 73 into engagement with the notches 69. Thus, the frictional force exerted by the detent mechanism is sufficient to normally prevent relative rotation of the rotation grip 60 with respect to the stabilizing handle 50, but this frictional force is sufficiently light as to permit the physician easily overcome it when he wishes to rotate the rotation grip 60 with respect to the stabilizing handle 50. The particular depiction of the detent mechanism is somewhat schematic, and it will be appreciated that the relative size and orientation of the various components (including the depth and slant of the notches 69 and the shape of the tip portion 73) can be adjusted and modified to produce the desired balance of forces. (Also, for purposes of clarity, in FIG. 25 the catheter 120 and the structures contained within the catheter 120 are not shown.)

Figure 26:
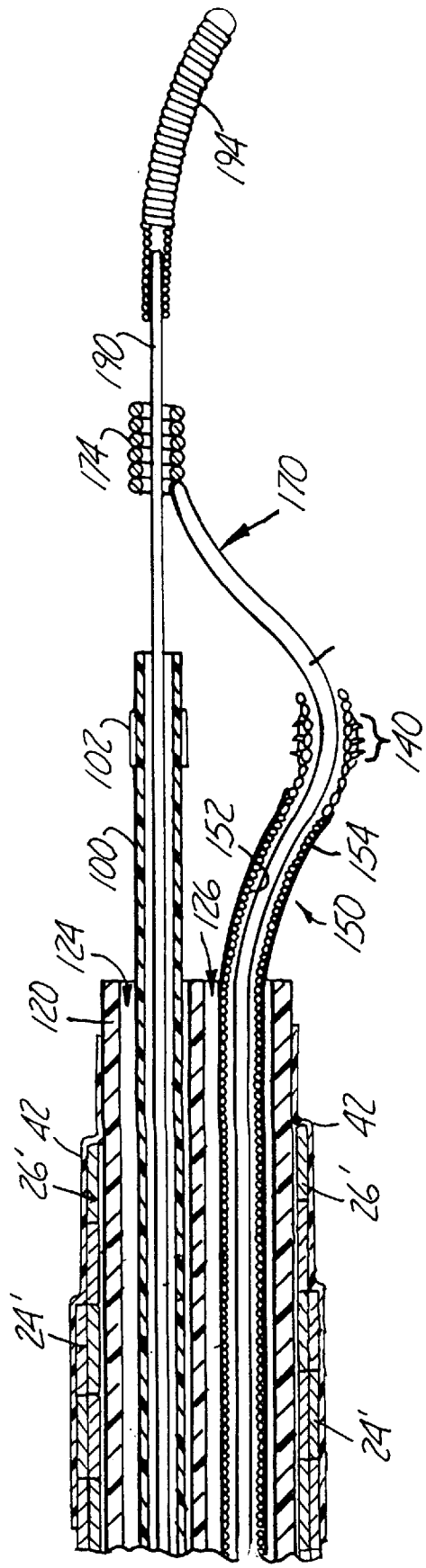
FIG. 26 is a partial cross-sectional, broken-away view of the distal end portion of the invention utilized in connection with another embodiment of a directional rotational atherectomy device.

FIG. 26 depicts the distal end portion of a two layer interference fit torquing sheath utilized in connection with another embodiment of directional rotational atherectomy device. This type of directional rotational atherectomy device is described in detail in U.S. Pat. No. 5,360,432 (Shturman), which is incorporated herein by reference. This device utilizes a dual lumen catheter 120. A conventional guide wire 190 having a conventional helically wound distal tip portion 194 is disposed in a first one of the lumens 124, and a flexible drive shaft 150 is disposed over and is rotatable over a positioning wire 170 in the other lumen 126. The positioning wire 170 is slidably secured at its distal end 174 to the guide wire 190 so that the positioning wire 170 can be moved proximally and distally with respect to the guide wire 190. The positioning wire 170 includes a distal positioning segment having a predetermined shape. The drive shaft 150 includes a segment near its distal end which is coated with an abrasive material to define an abrasive segment 140 of the drive shaft 150. When the drive shaft's abrasive segment 140 is positioned along the predetermined curved shape of the positioning wire's positioning segment, the positioning segment positions the abrasive segment 140 of the drive shaft 150 laterally away from the guide wire 190, thus giving control over the lateral position of the abrasive segment 140 within the artery. The device therefore allows selective removal of tissue from one side of an artery permitting selective treatment of eccentric stenotic lesions.

The atherectomy device depicted in FIG. 26 is particularly well suited for use with intravascular ultrasound imaging technology. As illustrated in FIG. 26, an intravascular ultrasound imaging catheter 100 is positioned over the guide wire 90, extending distally out of the first lumen 124 of the catheter 120. Ultrasound transducer elements 102 (indicated schematically) are positioned adjacent to the abrasive segment 140 in the same cross-sectional plane of the passageway, permitting imaging of the thickness and composition of the atherosclerotic plaque, the relative position of the abrasive segment 140 of the drive shaft 150 with respect to the stenotic tissue, and imaging of the stenotic tissue as it is being removed. Other known types of ultrasonic catheters (different from the type shown in FIG. 26) also may be utilized. Guide wires carrying ultrasound transducers, and other types of imaging devices could also be utilized.

All of the above embodiments of the invention have depicted the distal end of the torquing sheath 20 as being essentially permanently secured to the distal end portion of the medical device. In some circumstances, however, it may be desirable to be able to remove the torquing sheath once the medical device has been properly navigated to its site of usage. For example, in many medical procedures a guide wire is initially advanced to a location of interest, and then other medical devices are advanced over the guide wire to the site of interest. Physicians very often form a curve at the most distal flexible portion of a guide wire to facilitate steering the guide wire into the branch vessel of interest. Good torque characteristics of the guide wire are important for such steering. In use, however, such guide wires are often subject to less than desirable rotational control and distal end "whipping". Techniques for improving the torque-conveying ability of such guide wires may involve increasing the diameter of the guide wire, which in turn may reduce its lateral flexibility.

The invention may be utilized to temporarily increase the rotational control of a guide wire while navigating the guide wire to an area of interest. Upon reaching the desired area, the entire guide wire (except for its distal tip portion) may be restored to its original small diameter and lateral flexibility prior to advancing a medical device (e.g., a rotational atherectomy device) over the guide wire.

Figure 27:
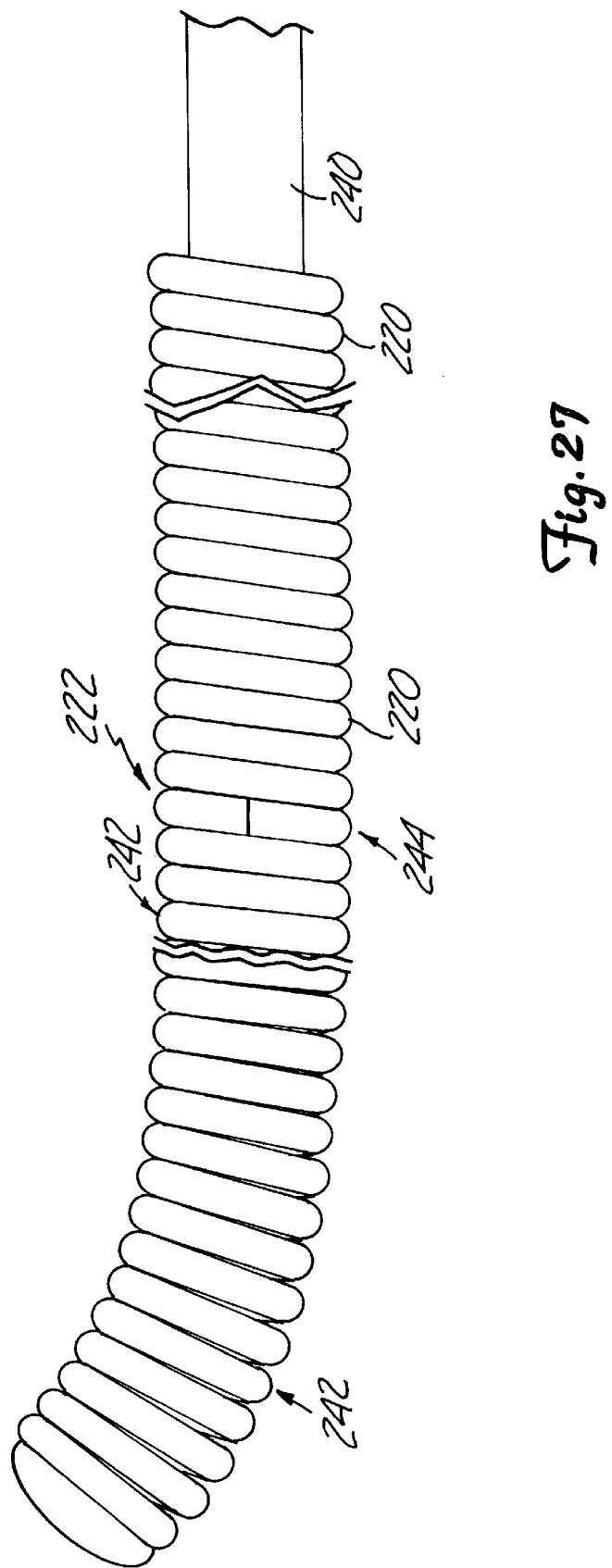
FIG. 27 is a broken-away view of another embodiment of the invention utilizing a torquing sheath having a distal end which is removably engageable with the proximal end of the distal portion of the medical device.
Figure 28:
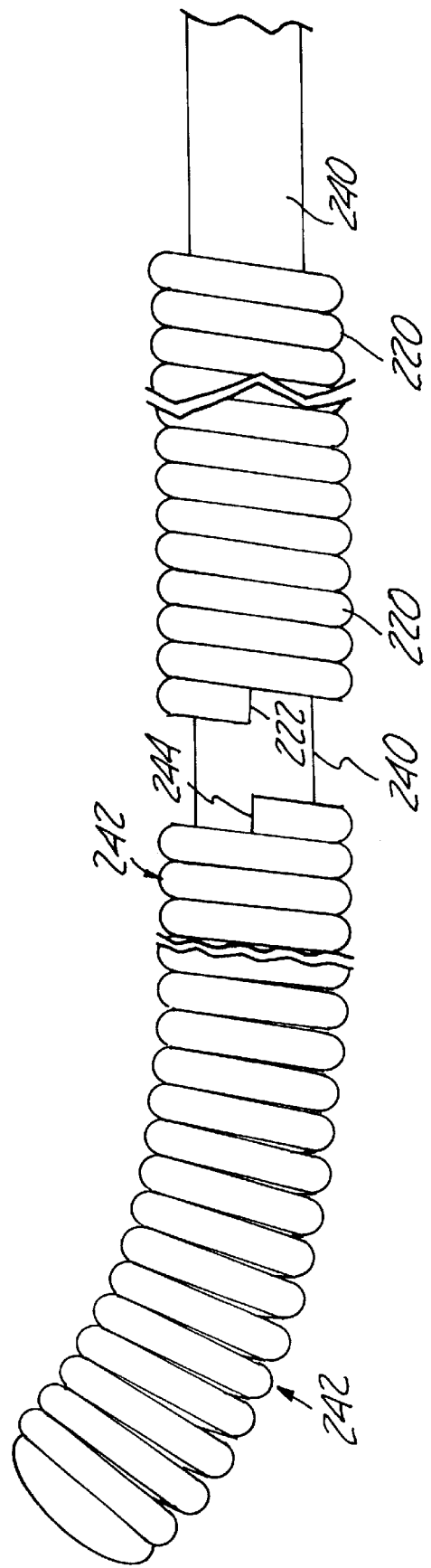
FIG. 28 is a broken-away view similar to FIG. 27, depicting the torquing sheath in a moved position.

FIG. 27 depicts a guide wire having a conventional coiled, flexible distal tip portion 242 which has a diameter slightly larger than the diameter of the generally solid shaft portion 240 of the guide wire. A helically wound wire torquing sheath 220 is disposed over the shaft portion 240 of the guide wire. The torquing sheath 220 terminates in a distal end 222 having a face which abuts a complementary face on the proximal end 244 of the guide wire's coiled, flexible distal tip portion 242. These complementary faces, when abutting each other, lie in a plane that is generally parallel to the longitudinal axis of the medical device. Thus, the two coils are sized and positioned so that, viewed from the proximal end, counterclockwise rotation of the torquing sheath will cause the distal end 222 of the torquing sheath to push against the proximal end 244 of the coiled, flexible distal tip portion 242 of the guide wire, thus rotating the distal tip portion of the guide wire counterclockwise. When the positioning function of the torquing sheath 220 has been completed, it may be withdrawn proximally, as shown in FIG. 28, leaving the guide wire in its desired position. The guide wire shaft 240 can be made with a very small diameter and significant flexibility, so that after complete withdrawal of the torquing sheath 220, other low-profile medical devices may be advanced over the shaft 240 of the guide wire to perform the desired medical procedure.

Figure 30:
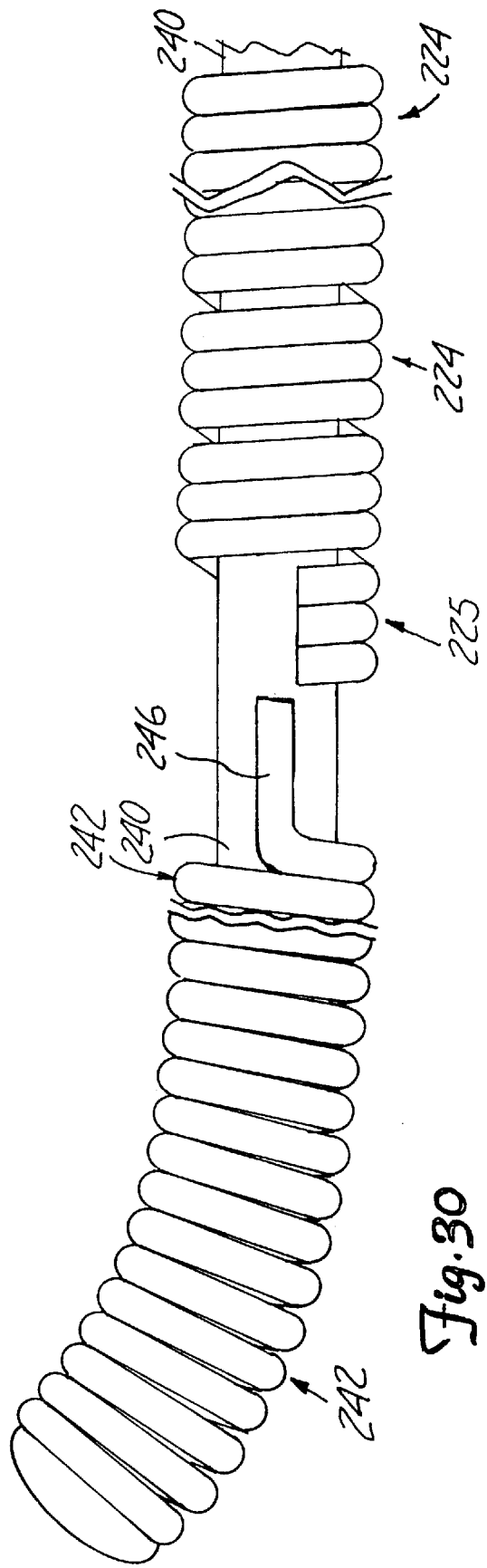
FIG. 30 is a broken-away view similar to FIG. 29, depicting the torquing sheath in a moved position.

FIG. 29 depicts an alternate mechanical abutment of the distal end of the torquing sheath with the proximal end of the coiled, flexible distal tip portion. In this embodiment, the torquing sheath 224 is tri-filar, and the proximal end of the coiled, flexible distal tip portion 242 includes a proximally extending rib 246 against which the ends 225 of the torquing sheath wires may abut. Preferably this rib is formed by bending and proximally extending a short segment 246 of the wire forming the guide wire's distal coiled tip portion. If desired, the proximal extending segment 246 may be provided with an indentation 247, and the ends 225 of the torquing sheath wires may be so configured, as shown in FIG. 29A, to provide a modest amount of mechanical engagement tending to interlock the two components so long as rotational force is exerted on the torquing sheath 224 against the proximally extending segment 246 of the distal tip portion of the guide wire. As depicted in FIG. 30, and as described above with respect to FIGS. 27–28, once the positioning function of the torquing sheath 224 has been completed, it may be withdrawn proximally, leaving the guide wire in its desired position.

FIG. 31 depicts a two-layer, torquing sheath having counter-wound outer 224 and inner 227 layers. The ends 225 and 228 of the outer 224 and inner 227 layers have faces which abut opposite sides of the proximally extending short segment 246, these faces lying generally in planes that are parallel to the longitudinal axis of the guide wire. In the preferred embodiment shown in FIG. 31, the inner 227 and outer 224 layers of the torquing sheath are in an interference fit, and made from generally rectangular wire. Wires of other cross-sectional shapes may also be used. The two-layer embodiment of the torquing sheath permits rotation of the distal end of the guide wire in either clockwise or counter-clockwise directions. FIGS. 31A and 31B depict two alternate embodiments for providing a modest amount of mechanical engagement tending to interlock the torquing sheath with the guide wire.

FIG. 32 depicts another embodiment utilizing a torquing sheath 260 having a distal end which is removably engageable with a slot 241 formed in the distal portion of the shaft 240 of the guide wire. In FIG. 32, the distal end of the wire from which the torquing sheath 260 is constructed has a radially inwardly formed finger 262 which engages the slot 241 to rotationally interlock the torquing sheath 260 with the shaft 240 of the guide wire. As FIG. 32A illustrates, however, when the torquing sheath 260 is withdrawn proximally with respect to the guide wire, the finger 262 of the torquing sheath 260 disengages from the slot 241 to permit removal of the torquing sheath.

Figure 32D:
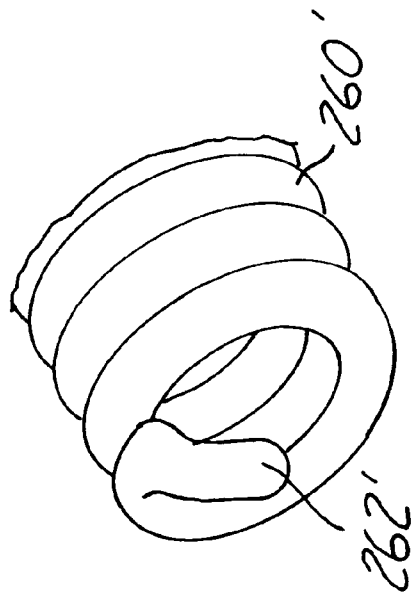
FIGS. 32C and 32D depict in perspective, broken-away views, alternate configurations for the distal end of the torquing sheath.
Figure 32B:
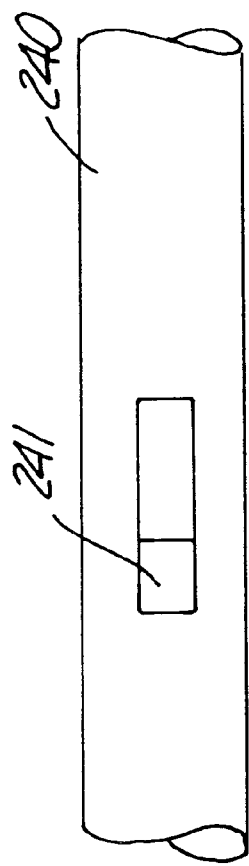
FIG. 32B is a broken-away, plan view of the slot.
Figure 32C:
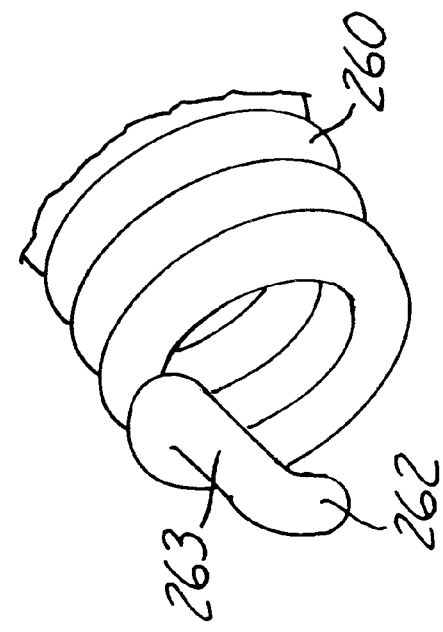

FIG. 32B shows the slot 241 in plan view. FIGS. 32C and 32D depict alternate configurations for the distal end of the torquing sheath. In FIG. 32C, the finger 262 is carried at the end of a distally extending arm 263. In FIG. 32D, the finger 262' extends radially inwardly immediately at the end of the wire coil of the torquing sheath 260'. Other suitable configurations can similarly be utilized.

FIG. 33 depicts yet another embodiment utilizing a high friction material 230 deposited on the distal end of the torquing sheath 220 and a similar or complementary material 248 deposited on the proximal end of the flexible, coiled distal tip portion of the guide wire. In FIG. 33, the materials 230 and 248 are depicted as being essentially the same material, such as, e.g., diamond grit or soft plastics or rubbers. Alternately, a rough material may be placed on only the distal end of the torquing sheath, with a complementary relatively soft material (such as, e.g., silicone) placed on the proximal end of the flexible, coiled distal tip portion of the guide wire. In yet another variation, instead of depositing high friction material on the distal end of the torquing sheath, this end may merely be provided with a roughened surface. Furthermore, these configurations may also be reversed, providing the proximal end of the flexible, coiled distal tip portion of the guide wire with the high friction surface, and the distal end of the torquing sheath with a complementary relatively soft material. Other suitable variations for providing a high friction interface between these two components will be readily apparent to those skilled in the art. With this embodiment, the physician exerts a modest distal force on the torquing sheath 220 as the torquing sheath 220 is rotated to engage the torquing sheath 220 with the flexible, coiled distal tip portion 242 of the guide wire, FIG. 34 depicts another mechanism for engaging the torquing sheath 220 with the flexible, coiled distal tip portion 242 of the guide wire. In this embodiment, the torquing sheath 220 includes a distal end fitting 232 having distally extending protrusions 233, and the coiled distal tip portion 242 of the guide wire includes a proximal end fitting 250 having complementary recesses 251 for receiving therein such protrusions 233. FIGS. 34A and 34B illustrate two variations on the size and shape of the protrusions and recesses, providing varying degrees of mechanical interlocking between the two components. Alternately, protrusions/recesses could be reversed, with the protrusions being carried by the guide wire's distal tip portion, and the recesses being formed in a distal end fitting on the torquing sheath. (For purposes of illustration, the angles of the protrusions 233 and recesses 251 in FIGS. 34A and 34B are somewhat exaggerated.) FIG. 35 illustrates use of this protrusion/recess mechanism with a torquing sheath comprising polymeric tubing 235 reinforced with wire braiding 236.

Figure 36:
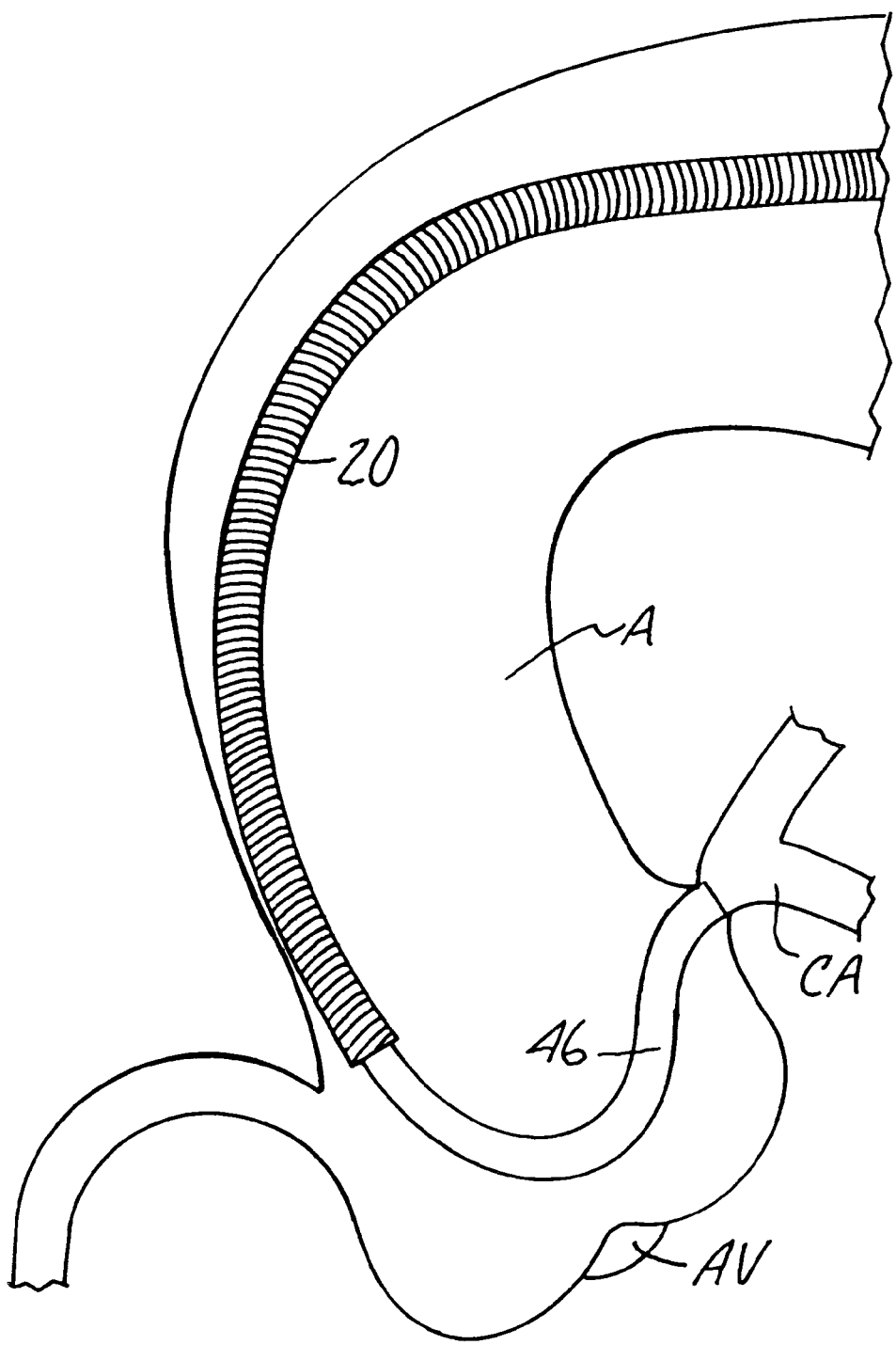
FIG. 36 is a somewhat schematic view of another embodiment of the invention utilizing a torquing sheath to position a guiding catheter at the entry into a coronary artery from within the ascending portion of the aorta.

FIG. 36 depicts another application of the invention. In this embodiment a torquing sheath 20 is disposed over a guiding catheter 46 which has a curved distal end portion. The guiding catheter 46 is depicted as being positioned in the ascending portion of the aorta "A", with its distal tip positioned at the entry to a coronary artery "CA" located just superior to the aortic valve "AV". The curve in commercially available curved guiding catheters assists the physician in orienting the distal tip of the catheter with respect to the entry to the coronary artery, but the physician must still manually rotate the proximal end of the catheter to obtain the proper rotational position of the distal tip of the catheter within the aorta. Wire braiding is used to improve the torque-conveying ability of such guiding catheters, but they are nevertheless often still susceptible to the distal end "whipping" and over-rotating shortcomings described above. The torquing sheath 20 of the invention provides increased control over the rotational position of the guiding catheter 46 in positioning it at the entry to a coronary artery or other desired bodily passageway.

Figure 37:
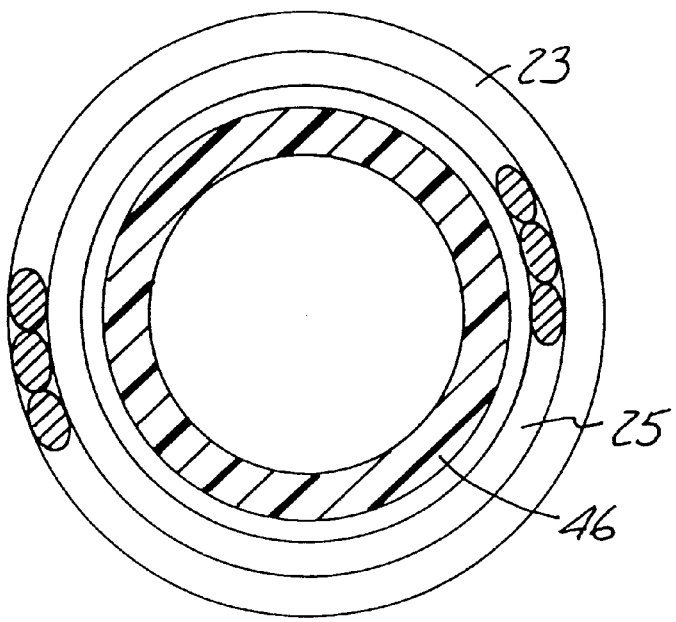
FIG. 37 is a cross-sectional view of a two-layer torquing sheath utilized with a guiding catheter.
Figure 38:
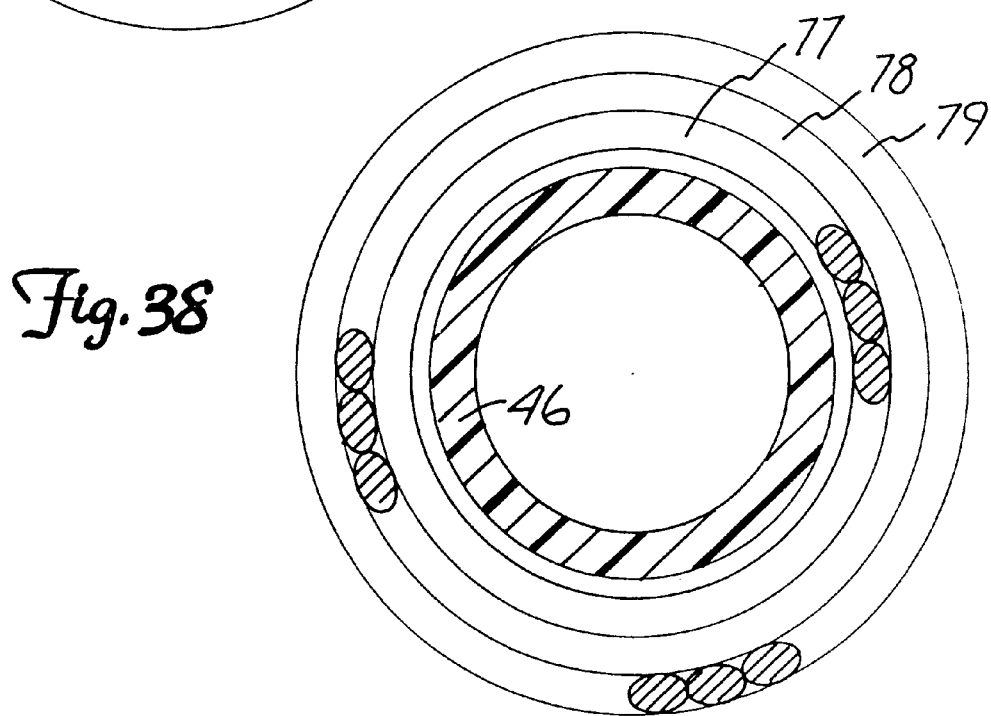
FIG. 38 is a cross-sectional view similar to FIG. 37 depicting a three-layer torquing sheath utilized with a guiding catheter.

FIGS. 37 and 38 depict cross-sectional views of two and three-layer interference fit torquing sheaths used with a guiding catheter 46 of the type depicted in FIG. 36. In FIG.

37 the outer layer is designated generally as 23, and the inner layer generally as 25; in FIG. 38 the outer layer is designated as 79, the intermediate layer as 78, and the inner layer as 77.

FIG. 39 depicts an alternate embodiment of the invention where the medical device comprises a catheter 91 with a conventional guide wire 90 disposed therein. The torquing sheath in this embodiment comprises a flexible torque tube 88, optionally reinforced by a wire braid 89. A short section of heat shrinkable tube 42 secures the distal end portion of the flexible torque tube 88 to the distal end portion of the catheter 91.

FIG. 40 depicts yet another embodiment in which a two-layer helically wound torquing sheath 94 is disposed inside of (rather than outside of) a medical device (in this case, a conventional catheter) 95.

Figure 41:
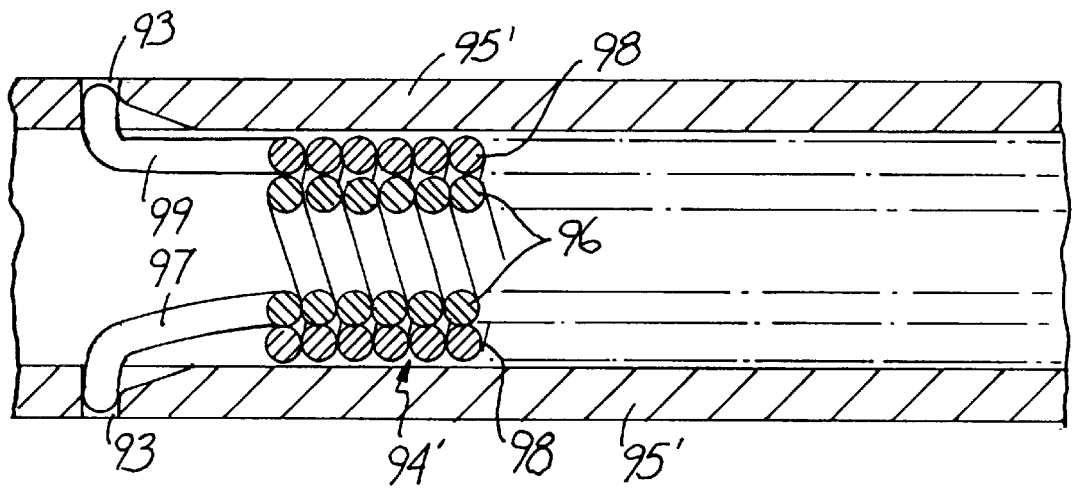
FIG. 41 is a longitudinal cross-sectional view of another embodiment of the invention utilizing a disengageable torquing sheath disposed inside of the medical device.
Figure 42:
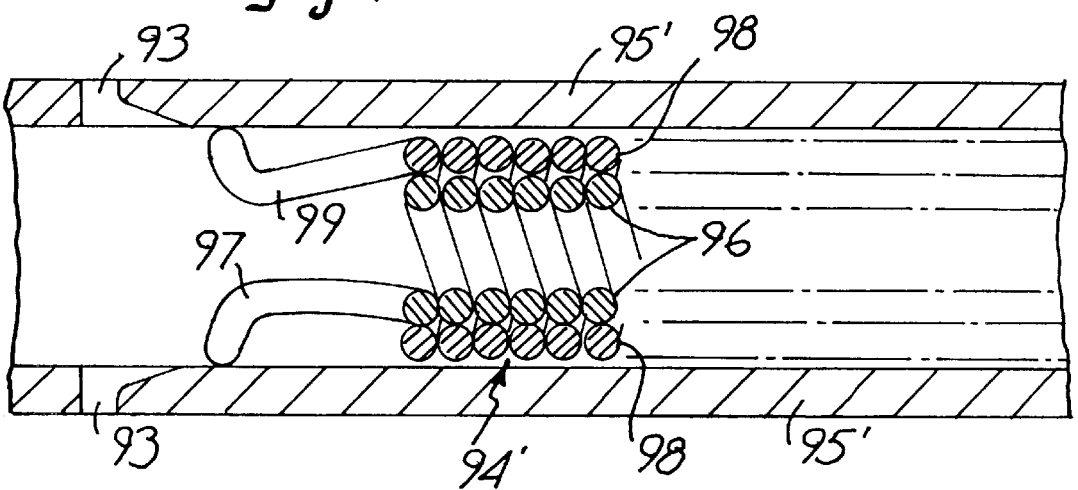
FIG. 42 is a longitudinal cross-sectional view similar to FIG. 41 depicting the torquing sheath in a moved position.

FIG. 41 depicts an embodiment similar to FIG. 40, but with a mechanism for detachably interlocking the torquing sheath 94' to the catheter 95'. The distal end of each of the wire layers 96 and 98 of the torquing sheath are formed into resilient, radially extending tab portions 97 and 99, respectively. These tab portions engage complementary apertures 93 formed in the wall of the catheter 95', The torquing sheath 94' may be withdrawn proximally from the catheter 95', as shown in FIG. 42, once the catheter is properly positioned in the site of interest.

Figure 43:
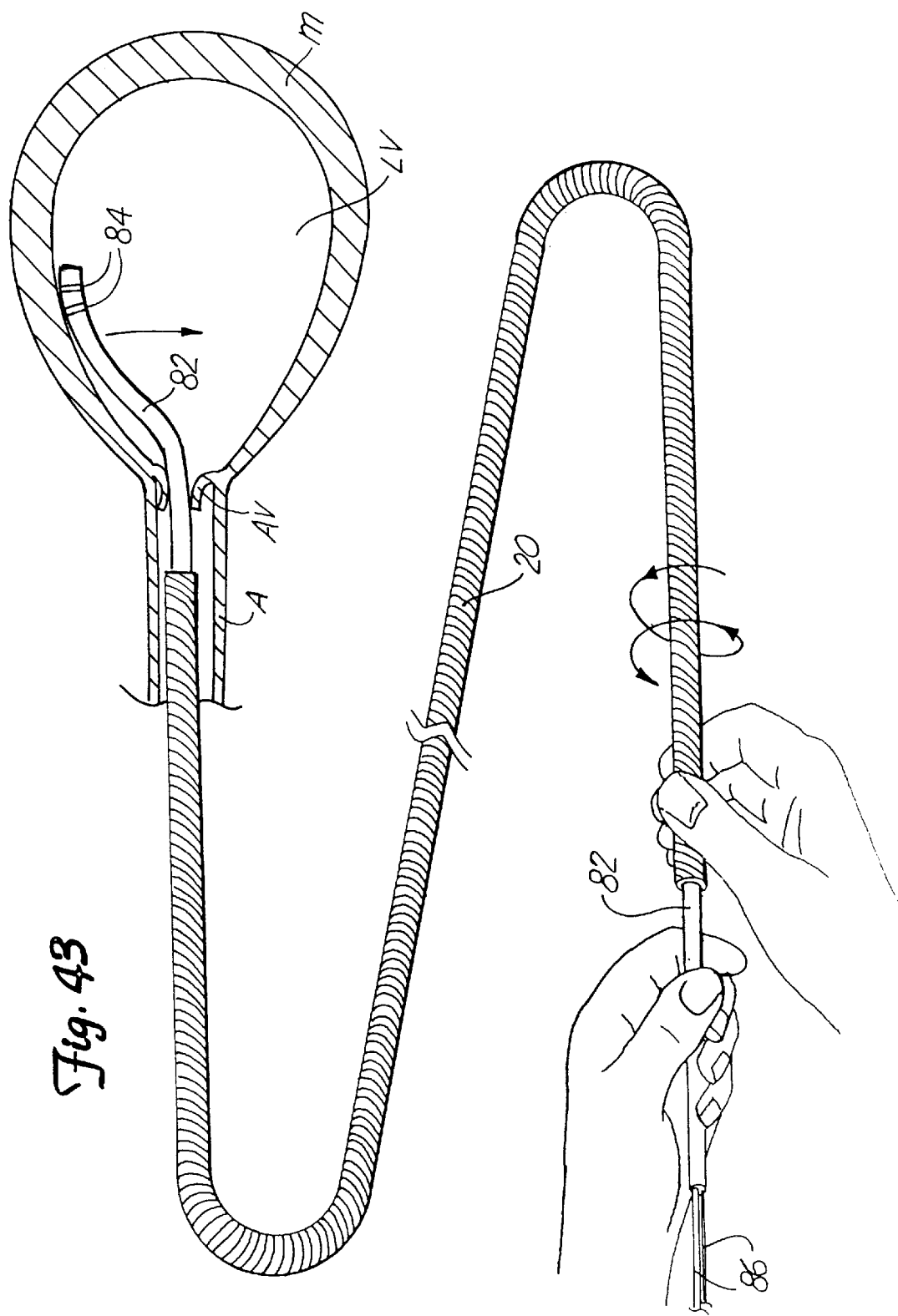
FIG. 43 is a somewhat schematic representation of a device of the invention being utilized to perform a diagnostic cardiac mapping procedure or a therapeutic radiofrequency (RF) catheter cardiac ablation procedure.

FIG. 43 depicts yet another application, the use of the invention for mapping the electrical potentials of a patient's myocardium, and for use in radiofrequency (RF) cardiac ablation procedures. In FIG. 43 a simplified form of the device is illustrated somewhat schematically for use, e.g., in the left ventricle. The torquing sheath 20 is disposed over a catheter 82 having a pre-formed curve (or a controllable steering mechanism) in its distal end portion. The distal end of the catheter 82 is inserted, through the aorta "A" and aortic valve "AV" into the left ventricle "LV". The curve in the distal portion of the catheter 82 is shaped so as to permit manipulation of catheter 82 to locate the electrodes 84 at various desired sites within the ventricle. The catheter 82 and electrodes 84 (with associated electrical leads 86) may be of the type used to map the electrical potential of the myocardium at various sites within the ventricle, or may be of the type used for radiofrequency (RF) cardiac ablation.

Use of the invention to control the rotational orientation of a distal end portion of a flexible, elongated device is quite straightforward in light of the above descriptions of various embodiments. When the physician desires to rotate the distal end of the device to a particular location or orientation, the proximal end of the torquing sheath may be rotated (relative to the proximal end portion of the elongated device) in the desired direction, conveying torque to the distal end of the torquing sheath and hence to the distal end portion of the elongated device. Since the proximal end portion of the elongated device is being held, and, therefore, is prevented from rotating, the torque conveyed by the torquing sheath to the distal end portion of the elongated device causes the distal end portion of the elongated device to begin rotating, but immediately the elongated device's own resistance to twisting gives rise to an increasing counter-balancing torque built up in the elongated device. Thus, a given amount of rotation of the proximal end of the torquing sheath will produce some degree of rotation of the distal end portion of the elongated device and also will build up a counter-balancing torque in the elongated device.

The counter-balancing torque force built up in the elongated device tends to reduce or even eliminate distal end "whip" often experienced with conventional catheters, guide wires and other probes—i.e., whip which results from the sudden release of torque built-up in the device as its proximal end is rotated and frictional force at its distal end and/or along its length is finally overcome. In the present invention, in contrast to these prior art devices (e.g., conventional guide wires and catheters, including guiding catheters), the counter-balancing torque force built up in the elongated device is in the same direction as the frictional force, and this counter-balancing force can be created at levels higher than the frictional force. When the counter-balancing torque in the elongated device is larger than frictional force encountered at the distal end and/or along the length of the device, whip is significantly reduced or eliminated because the sudden release of any built-up frictional torque is small in relation to the counter-balancing torque of the catheter. Moreover, since the proximal end portion of the elongated device is being held by the physician (i.e., it is not permitted to rotate), any tendency of the device to "whip" due to the release of frictional force will merely increase the magnitude of the counter-balancing torque built up in the elongated device—i.e., immediately increasing the magnitude of the force opposing the tendency to "whip."

In certain procedures it may be desired to rotate the distal end portion of the elongated medical device through a substantial arc—even through multiple 360° turns. In such cases, the torquing sheath may be rotated, e.g., for a certain number of turns, producing a certain degree of distal rotation and creating a certain level of counter-balancing torque in the elongated medical device. The proximal end portion of the elongated medical device may then be rotated in the same direction as the torquing sheath, releasing some (or, if desired, all) of the counter-balancing torque already built up in the elongated medical device Since this process may be repeated as many times as desired, continuous, multiple 360° turns of the elongated medical device are thus possible. If desired, a mechanical slip clutch could be utilized in a handle for the device of the invention such that the proximal end portion of the elongated medical device would automatically be permitted to rotate after a certain degree of counter-balancing torque had been built up in the elongated medical device as a result of a certain degree of relative rotation of the proximal end of the torquing sheath with respect to the proximal end portion of the elongated medical device.

While a preferred embodiment of the present invention has been described, it should be understood that various changes, adaptations and modifications may be made therein without departing from the spirit of the invention and the scope of the appended claims.

What is claimed is:

1. A rotatable medical apparatus comprising:

a flexible, elongated medical device advanceable into a bodily passageway or cavity, the medical device having proximal, intermediate and distal portions, the distal portion including a rotationally positionable element; and a flexible torquing sheath extending along a substantial length of the elongated medical device, the sheath having proximal and distal ends and an intermediate segment;

the proximal end and the intermediate segment of the torquing sheath being rotatable with respect to the proximal portion of the medical device, the distal end of the torquing sheath being secured to the distal portion of the medical device to prevent relative rotation of the distal end of the torquing sheath and the distal portion of the medical device with respect to each other so that rotation of the proximal end of the torquing sheath with respect to the proximal portion of the medical device conveys torque to the distal end of the torquing sheath and, therefore, to the distal portion of the medical device, thereby rotating the distal portion of the medical device, permitting a user to rotationally position the rotationally positionable element;

a stabilizing handle secured to the proximal portion of the medical device and a rotation grip secured to the proximal end of the torquing sheath, the rotation grip being rotatable with respect to the stabilizing handle to permit selective rotation of the proximal end of the torquing sheath with respect to the proximal portion of the medical device, thereby rotating the distal portion of the medical device with respect to the proximal portion of the medical device;

means for substantially preventing relative longitudinal movement of the rotation grip with respect to the stabilizing handle, a relative rotation indicator indicating the extent of relative rotation of the rotation grip with respect to the stabilizing handle, the relative rotation indicator comprising an internally threaded collar disposed within the rotation grip and being received over complementary external threads formed in the stabilizing handle, the collar carrying a radially outwardly extending pin received in a longitudinal slot formed in the rotation grip, longitudinal movement of the collar and pin thereby indicating the extent of relative rotation of the rotation grip with respect to the stabilizing handle.

2. The medical apparatus of claim 1 further including visible markings on the rotation grip along the longitudinal slot providing a quantifiable indication of the extent of relative rotation of the rotation grip with respect to the stabilizing handle.

3. A rotatable medical apparatus comprising:
a flexible, elongated medical device advanceable into a bodily passageway or cavity, the medical device having proximal, intermediate and distal portions; and
a flexible torquing sheath extending along a substantial length of the elongated medical device, the sheath having proximal and distal ends and an intermediate segment;
the proximal end and the intermediate segment of the torquing sheath being rotatable with respect to the medical device, the distal end of the torquing sheath being secured to the distal portion of the medical device so that rotation of the proximal end of the torquing sheath with respect to the proximal portion of the medical device conveys torque to the distal end of the torquing sheath and, therefore, to the distal portion of the medical device, thereby rotating the distal portion of the medical device;
a stabilizing handle secured to the proximal portion of the medical device and a rotation grip secured to the proximal end of the torquing sheath, the rotation grip being rotatable with respect to the stabilizing handle to permit selective rotation of the proximal end of the torquing sheath with respect to the proximal portion of the medical device, thereby rotating the distal portion of the medical device with respect to the proximal portion of the medical device; and
a coil spring interposed between a surface of the rotation grip and a surface of the stabilizing handle, the spring inhibiting free rotational movement of the rotation grip with respect to the stabilizing handle.

4. A rotatable medical apparatus comprising:
a flexible, elongated medical device advanceable into a bodily passageway or cavity, the medical device having proximal, intermediate and distal portions; and
a flexible torquing sheath extending along a substantial length of the elongated medical device, the sheath having proximal and distal ends and an intermediate segment;
the proximal end and the intermediate segment of the torquing sheath being rotatable with respect to the medical device, the distal end of the torquing sheath being secured to the distal portion of the medical device so that rotation of the proximal end of the torquing sheath with respect to the proximal portion of the medical device conveys torque to the distal end of the torquing sheath and, therefore, to the distal portion of the medical device, thereby rotating the distal portion of the medical device;
a stabilizing handle secured to the proximal portion of the medical device and a rotation grip secured to the proximal end of the torquing sheath, the rotation grip being rotatable with respect to the stabilizing handle to permit selective rotation of the proximal end of the torquing sheath with respect to the proximal portion of the medical device, thereby rotating the distal portion of the medical device with respect to the proximal portion of the medical device; and
a generally concave disk-shaped spring interposed between a surface of the rotation grip and a surface of the stabilizing handle, the spring inhibiting free rotational movement of the rotation grip with respect to the stabilizing handle.

5. A rotatable medical apparatus comprising;
a flexible, elongated medical device advanceable into a bodily passageway or cavity, the medical device having proximal, intermediate and distal portions, the distal portion including a rotationally positionable element; and
a flexible torquing sheath extending along a substantial length of the elongated medical device, the sheath having proximal and distal ends and an intermediate segment;
the proximal end and the intermediate segment of the torquing sheath being rotatable with respect to the proximal portion of the medical device, the distal end of the torquing sheath being secured to the distal portion of the medical device to prevent relative rotation of the distal end of the torquing sheath and the distal portion of the medical device with respect to each other so that rotation of the proximal end of the torquing sheath with respect to the proximal portion of the medical device conveys torque to the distal end of the torquing sheath and, therefore, to the distal portion of the medical device, thereby rotating the distal portion of the medical device, permitting a user to rotationally position the rotationally positionable element;
a stabilizing handle secured to the proximal portion of the medical device and a rotation grip secured to the proximal end of the torquing sheath, the rotation grip being rotatable with respect to the stabilizing handle to permit selective rotation of the proximal end of the torquing sheath with respect to the proximal portion of the medical device, thereby rotating the distal portion of the medical device with respect to the proximal portion of the medical device; and
a detent mechanism interconnecting the stabilizing handle and the rotation grip for inhibiting relative rotation of the rotation grip with respect to the stabilizing handle, the detent mechanism comprising a series of notches formed in the rotation grip, and a lever carried by the stabilizing handle, the lever having a tip portion that is engageable with the notches in the rotation grip, the lever being spring biased so that the tip portion is urged into engagement with the notches.

6. A rotatable medical apparatus comprising:

a flexible, elongated medical device advanceable into a bodily passageway or cavity, the medical device having proximal, intermediate and distal portions, the distal portion including a rotationally positionable element; and a flexible torquing sheath extending along a substantial length of the elongated medical device, the sheath having proximal and distal ends and an intermediate segment;

the proximal end and the intermediate segment of the torquing sheath being rotatable with respect to the proximal portion of the medical device, the distal end of the torquing sheath being secured to the distal portion of the medical device to prevent relative rotation of the distal end of the torquing sheath and the distal portion of the medical device with respect to each other so that rotation of the proximal end of the torquing sheath with respect to the proximal portion of the medical device conveys torque to the distal end of the torquing sheath and, therefore, to the distal portion of the medical device, thereby rotating the distal portion of the medical device, permitting a user to rotationally position the rotationally positionable element;

the medical device comprising a directional rotational atherectomy device having:

an elongated catheter having at least first and second lumens and a distal end;

a guide wire receivable in the first lumen of the catheter and extending distally therefrom;

a flexible, elongated drive shaft having proximal and distal ends and a central lumen, the drive shaft being receivable in the second lumen of the catheter and being longitudinally movable therein, the drive shaft further including a segment, near its distal end, coated with an abrasive material to define an abrasive segment of the drive shaft; and a positioning wire, which is receivable in the drive shaft lumen and around which the drive shaft may be rotated, the positioning wire having a distal end and means for slidably securing the distal end of the positioning wire about the guide wire distally of the distal end of the catheter so that the positioning wire can be moved proximally and distally with respect to the guide wire, the positioning wire further including a distal positioning segment having a predetermined shape, the drive shaft being movable longitudinally with respect to the positioning wire and the catheter to selectively locate the drive shaft's abrasive segment along the predetermined shape of such positioning segment of the positioning wire to selectively position the abrasive segment laterally of the guide wire.

7. The medical apparatus of claim 6 further comprising an intravascular ultrasound imaging catheter disposed over the guide wire in the first lumen and extending distally out of the first lumen of the catheter.

8. The medical apparatus of claim 7 wherein the ultrasound imaging catheter is positioned so that its ultrasound transducer elements are positioned adjacent to the abrasive segment of the drive shaft.

9. The medical apparatus of claim 6 wherein the guide wire is an ultrasound imaging guide wire carrying one or more ultrasound transducers.

10. A rotatable medical apparatus comprising:

a flexible, elongated medical device advanceable into a bodily passageway or cavity, the medical device having proximal, intermediate and distal portions, the distal portion including a rotationally positionable element; and a flexible torquing sheath extending along a substantial length of the elongated medical device, the sheath having proximal and distal ends and an intermediate segment;

the proximal end and the intermediate segment of the torquing sheath being rotatable with respect to the proximal portion of the medical device, the distal end of the torquing sheath being secured to the distal portion of the medical device to prevent relative rotation of the distal end of the torquing sheath and the distal portion of the medical device with respect to each other so that rotation of the proximal end of the torquing sheath with respect to the proximal portion of the medical device conveys torque to the distal end of the torquing sheath and, therefore, to the distal portion of the medical device, thereby rotating the distal portion of the medical device, permitting a user to rotationally position the rotationally positionable element;

the medical device comprising a catheter having a distal end portion having electrodes for mapping the electrical potentials of a patient's myocardium.

11. A rotatable medical apparatus comprising:

a flexible, elongated medical device advanceable into a bodily passageway or cavity, the medical device having proximal, intermediate and distal portions, the distal portion including a rotationally positionable element; and a flexible torquing sheath extending along a substantial length of the elongated medical device, the sheath having proximal and distal ends and an intermediate segment;

the proximal end and the intermediate segment of the torquing sheath being rotatable with respect to the proximal portion of the medical device, the distal end of the torquing sheath being secured to the distal portion of the medical device to prevent relative rotation of the distal end of the torquing sheath and the distal portion of the medical device with respect to each other so that rotation of the proximal end of the torquing sheath with respect to the proximal portion of the medical device conveys torque to the distal end of the torquing sheath and, therefore, to the distal portion of the medical device, thereby rotating the distal portion of the medical device, permitting a user to rotationally position the rotationally positionable element;

the medical device comprising a catheter having a distal end portion having electrodes for myocardial ablation procedures.

12. A rotatable medical apparatus comprising:

a flexible, elongated medical device advanceable into a bodily passageway or cavity, the medical device having proximal, intermediate and distal portions; and a flexible torquing sheath extending along a substantial length of the elongated medical device the sheath having proximal and distal ends and an intermediate segment;

the distal end of the torquing sheath being removably engageable with the distal portion of the medical device, so that when the distal end of the torquing sheath is engaged with the distal portion of the medical device, rotation of the proximal end of the torquing sheath with respect to the proximal portion of the medical device conveys torque to the distal end of the torquing sheath and, therefore, to the distal portion of the medical device, thereby rotating the distal portion of the medical device;

the distal end of the torquing sheath being so configured and arranged as to be disengageable from the distal portion of the medical device, permitting the torquing sheath to be withdrawn proximally with respect to the medical device;

the distal portion of the medical device including a proximally extending rib, the torquing sheath comprising inner and outer layers of helically wound wire, the two layers being wound in opposite directions, the distal ends of the wires terminating in opposing faces oriented to abut against opposite sides of the rib to transmit torque from the distal end of the helically wound wires to the rib of the distal portion of the medical device.

13. The apparatus of claim 12 wherein the medical device has a longitudinal axis, the opposing faces of the distal end of the torquing sheath, when abutting the sides of the rib on the distal portion of the medical device, lying in one or more planes that are generally parallel to the longitudinal axis of the medical device.

14. The apparatus of claim 12 wherein the medical device is a guide wire, the distal portion of the guide wire including a helically wound wire, the proximally extending rib comprising a proximal end portion of the helically wound wire, such proximal end portion being oriented generally longitudinally with respect to the guide wire.

15. A rotatable medical apparatus comprising;

a flexible, elongated medical device advanceable into a bodily passageway or cavity, the medical device having proximal, intermediate and distal portions; and a flexible torquing sheath disposed concentrically within the medical device and extending along a substantial length of the elongated medical device, the sheath having proximal and distal ends and an intermediate segment;

the distal end of the torquing sheath being removably engageable with the distal portion of the medical device, so that when the distal end of the torquing sheath is engaged with the distal portion of the medical device, rotation of the proximal end of the torquing sheath with respect to the proximal portion of the medical device conveys torque to the distal end of the torquing sheath and, therefore, to the distal portion of the medical device, thereby rotating the distal portion of the medical device;

the torquing sheath including radially outwardly extending prongs engageable with radial apertures formed in the medical device, the prongs being so configured and arranged as to be disengageable from the apertures to permit the torquing sheath to be withdrawn proximally with respect to the medical device.

16. The apparatus of claim 15 wherein the prongs are made of a resilient material and are formed in a shape that resiliently urges them radially outwardly into engagement with the apertures in the medical device.

17. A high torque guide wire apparatus, comprising;

an elongated guide wire advanceable into a bodily passageway or cavity, the guide wire having proximal, intermediate and distal portions; and a flexible torquing sheath extending along a substantial length of the guide wire, the sheath having proximal and distal ends and an intermediate segment;

the distal end of the torquing sheath being removably engageable with the distal portion of the guide wire, so that when the distal end of the torquing sheath is engaged with the distal portion of the guide wire, rotation of the proximal end of the torquing sheath with respect to the proximal portion of the guide wire conveys torque to the distal end of the torquing sheath and, therefore, to the distal portion of the guide wire, thereby rotating the distal portion of the guide wire, the torquing sheath being disengageable from the distal portion of the guide wire by simply withdrawing it proximally with respect to the guide wire, the distal portion of the guide wire including a proximally extending rib, the torquing sheath comprising inner and outer helically wound wire layers, the two layers being wound in opposite directions, the distal ends of the wire layers terminating in laterally opposing faces oriented to abut against opposite sides of the rib to transmit torque from the distal ends of the helically wound wire layers to the rib of the distal portion of the guide wire.

18. The apparatus of claim 17 wherein the distal portion of the guide wire includes a helically wound wire, the proximally extending rib comprising a proximal end portion of the helically wound wire, such proximal end portion being oriented generally longitudinally with respect to the guide wire.

19. A high torque guide wire apparatus, comprising:

an elongated guide wire advanceable into a bodily passageway or cavity, the guide wire having proximal, intermediate and distal portions; and a flexible torquing sheath extending along a substantial length of the guide wire, the sheath having proximal and distal ends and an intermediate segment;

the distal end of the torquing sheath being removably engageable with the distal portion of the guide wire, so that when the distal end of the torquing sheath is engaged with the distal portion of the guide wire, rotation of the proximal end of the torquing sheath with respect to the proximal portion of the guide wire conveys torque to the distal end of the torquing sheath and, therefore, to the distal portion of the guide wire, thereby rotating the distal portion of the guide wire;

the distal end of the torquing sheath being so configured and arranged as to be disengageable from the distal portion of the guide wire to permit the torquing sheath to be withdrawn proximally with respect to the guide wire;

the torquing sheath including a distal end fitting having distally extending protrusions, and the distal portion of the guide wire including a proximal end fitting having complementary recesses for receiving therein such protrusions.

20. A high torque guide wire apparatus, comprising:

an elongated guide wire advanceable into a bodily passageway or cavity, the guide wire having proximal, intermediate and distal portions; and a flexible torquing sheath extending along a substantial length of the guide wire, the sheath having proximal and distal ends and an intermediate segment;

the distal end of the torquing sheath being removably engageable with the distal portion of the guide wire, so that when the distal end of the torquing sheath is engaged with the distal portion of the guide wire, rotation of the proximal end of the torquing sheath with respect to the proximal portion of the guide wire conveys torque to the distal end of the torquing sheath and, therefore, to the distal portion of the guide wire, thereby rotating the distal portion of the guide wire;

the distal end of the torquing sheath being so configured and arranged as to be disengageable from the distal portion of the guide wire to permit the torquing sheath to be withdrawn proximally with respect to the guide wire;

the distal portion of the guide wire including a proximal fitting having proximally extending protrusions, and the torquing sheath including a distal end fitting having complementary recesses for receiving therein such protrusions.

21. A high torque guide wire apparatus, comprising;

an elongated guide wire advanceable into a bodily passageway or cavity, the guide wire having proximal, intermediate and distal portions; and a flexible torquing sheath extending along a substantial length of the guide wire, the sheath having proximal and distal ends and an intermediate segment;

the distal end of the torquing sheath being removably engageable with the distal portion of the guide wire, so that when the distal end of the torquing sheath is engaged with the distal portion of the guide wire, rotation of the proximal end of the torquing sheath with respect to the proximal portion of the guide wire conveys torque to the distal end of the torquing sheath and, therefore, to the distal portion of the guide wire, thereby rotating the distal portion of the guide wire;

the distal end of the torquing sheath being so configured and arranged as to be disengageable from the distal portion of the guide wire to permit the torquing sheath to be withdrawn proximally with respect to the guide wire;

the guide wire including a shaft having an aperture in its distal portion, the torquing sheath including a radially inwardly extending finger which is engageable in the aperture to rotationally interlock the torquing sheath with the shaft of the guide wire, the finger being disengageable from the aperture to permit the torquing sheath to be withdrawn proximally with respect to the guide wire.

22. The apparatus of claim 21 wherein the aperture comprises a transverse slot.

23. A method of advancing a guide wire to a location of interest, comprising the steps of;

providing an elongated guide wire having proximal, intermediate and distal portions, the distal portion including a flexible distal tip portion;

providing a flexible torquing sheath that is advanceable over a substantial length of the guide wire, the torquing sheath having proximal and distal ends and an intermediate segment, the distal end of the torquing sheath being removably engageable with the distal portion of the guide wire;

advancing the guide wire and the torquing sheath into a bodily passageway;

rotating the proximal end of the torquing sheath with respect to the proximal portion of the guide wire to convey torque to the distal end of the torquing sheath and, therefore, to the distal portion of the guide wire to rotate the distal portion of the guide wire with respect to the proximal portion of the guide wire and, therefore, to rotationally position the flexible distal tip portion of the guide wire;

advancing the guide wire, together with the torquing sheath, further distally into the bodily passageway; and then withdrawing the torquing sheath proximally with respect to the guide wire to remove it from the guide wire.

24. The method of claim 23 further comprising the step of advancing another medical device over the guide wire into the bodily passageway after the torquing sheath has been completely withdrawn and removed from the guide wire.

25. The method of claim 23 wherein the torquing sheath is disengaged from the distal portion of the guide wire by withdrawing the torquing sheath proximally with respect to the guide wire.

* * * * *